(12) United States Patent
Hossainy et al.

(10) Patent No.: US 7,285,304 B1
(45) Date of Patent: Oct. 23, 2007

(54) FLUID TREATMENT OF A POLYMERIC COATING ON AN IMPLANTABLE MEDICAL DEVICE

(75) Inventors: Syed F. A. Hossainy, Fremont, CA (US); Ni Ding, San Jose, CA (US); Stephen D. Pacetti, San Jose, CA (US)

(73) Assignee: Advanced Cardiovascular Systems, Inc., Santa Clara, CA (US)

( * ) Notice: Subject to any disclaimer, the term of this patent is extended or adjusted under 35 U.S.C. 154(b) by 0 days.

(21) Appl. No.: 10/603,889

(22) Filed: Jun. 25, 2003

(51) Int. Cl.
*A61L 33/00* (2006.01)
(52) U.S. Cl. .................. 427/2.24; 427/2.25; 427/2.27
(58) Field of Classification Search ............... 427/2.24, 427/2.25, 2.27
See application file for complete search history.

(56) References Cited

U.S. PATENT DOCUMENTS

| | | |
|---|---|---|
| 3,687,135 A | 8/1972 | Stroganov et al. |
| 3,839,743 A | 10/1974 | Schwarcz |
| 3,900,632 A | 8/1975 | Robinson |
| 4,104,410 A | 8/1978 | Malecki |
| 4,110,497 A | 8/1978 | Hoel |
| 4,321,711 A | 3/1982 | Mano |
| 4,329,383 A | 5/1982 | Joh |
| 4,346,028 A | 8/1982 | Griffith |
| 4,596,574 A | 6/1986 | Urist |
| 4,599,085 A | 7/1986 | Riess et al. |
| 4,612,009 A | 9/1986 | Drobnik et al. |
| 4,633,873 A | 1/1987 | Dumican et al. |
| 4,656,083 A | 4/1987 | Hoffman et al. |
| 4,718,907 A | 1/1988 | Karwoski et al. |
| 4,722,335 A | 2/1988 | Vilasi |
| 4,723,549 A | 2/1988 | Wholey et al. |
| 4,732,152 A | 3/1988 | Wallstén et al. |
| 4,733,665 A | 3/1988 | Palmaz |
| 4,739,762 A | 4/1988 | Palmaz |
| 4,740,207 A | 4/1988 | Kreamer |
| 4,743,252 A | 5/1988 | Martin, Jr. et al. |
| 4,768,507 A | 9/1988 | Fischell et al. |
| 4,776,337 A | 10/1988 | Palmaz |
| 4,776,337 A | 10/1988 | Palmaz |
| 4,800,882 A | 1/1989 | Gianturco |
| 4,816,339 A | 3/1989 | Tu et al. |
| 4,818,559 A | 4/1989 | Hama et al. |
| 4,850,999 A | 7/1989 | Planck |
| 4,877,030 A | 10/1989 | Beck et al. |
| 4,878,906 A | 11/1989 | Lindemann et al. |
| 4,879,135 A | 11/1989 | Greco et al. |
| 4,882,168 A | 11/1989 | Casey et al. |
| 4,886,062 A | 12/1989 | Wiktor |
| 4,902,289 A | 2/1990 | Yannas |
| 4,941,870 A | 7/1990 | Okada et al. |
| 4,977,901 A | 12/1990 | Ofstead |
| 4,994,298 A | 2/1991 | Yasuda |
| 5,019,090 A | 5/1991 | Pinchuk |
| 5,028,597 A | 7/1991 | Kodama et al. |
| 5,059,211 A | 10/1991 | Stack et al. |
| 5,062,829 A | 11/1991 | Pryor et al. |
| 5,084,065 A | 1/1992 | Weldon et al. |
| 5,085,629 A | 2/1992 | Goldberg et al. |
| 5,100,429 A | 3/1992 | Sinofsky et al. |
| 5,104,410 A | 4/1992 | Chowdhary |
| 5,108,417 A | 4/1992 | Sawyer |
| 5,108,755 A | 4/1992 | Daniels et al. |
| 5,112,457 A | 5/1992 | Marchant |
| 5,123,917 A | 6/1992 | Lee |
| 5,156,623 A | 10/1992 | Hakamatsuka et al. |
| 5,163,951 A | 11/1992 | Pinchuk et al. |
| 5,163,952 A | 11/1992 | Froix |
| 5,163,958 A | 11/1992 | Pinchuk |
| 5,165,919 A | 11/1992 | Sasaki et al. |
| 5,167,614 A | 12/1992 | Tessmann et al. |
| 5,192,311 A | 3/1993 | King et al. |
| 5,197,977 A | 3/1993 | Hoffman, Jr. et al. |
| 5,234,456 A | 8/1993 | Silvestrini |
| 5,234,457 A | 8/1993 | Andersen |
| 5,236,447 A | 8/1993 | Kubo et al. |
| 5,272,012 A | 12/1993 | Opolski |
| 5,279,594 A | 1/1994 | Jackson |

(Continued)

FOREIGN PATENT DOCUMENTS

DE      44 07 079      9/1994

(Continued)

OTHER PUBLICATIONS

Anonymous, *Rolling Therapeutic Agent Loading Device for Therapeutic Agent Delivery or Coated Stent* (Abstract 434009), Res. Disclos. pp. 974-975 (Jun. 2000).

(Continued)

*Primary Examiner*—Bret Chen
(74) *Attorney, Agent, or Firm*—Squire, Sanders & Dempsey L.L.P.

(57) ABSTRACT

A method of manufacturing an implantable medical device including applying a composition to an implantable medical device, the composition including a polymer, an active agent and a solvent; allowing the solvent to evaporate to form a dry coating, the dry coating comprising less than about 2% residual fluid content (w/w); applying a fluid to the dry coating, the fluid being substantially free from any polymer; and allowing the fluid to evaporate from the coating.

46 Claims, 5 Drawing Sheets

U.S. PATENT DOCUMENTS

| | | |
|---|---|---|
| 5,282,860 A | 2/1994 | Matsuno et al. |
| 5,289,831 A | 3/1994 | Bosley |
| 5,290,271 A | 3/1994 | Jernberg |
| 5,292,516 A | 3/1994 | Viegas et al. |
| 5,298,260 A | 3/1994 | Viegas et al. |
| 5,300,295 A | 4/1994 | Viegas et al. |
| 5,306,286 A | 4/1994 | Stack et al. |
| 5,306,294 A | 4/1994 | Winston et al. |
| 5,306,501 A | 4/1994 | Viegas et al. |
| 5,328,471 A | 7/1994 | Slepian |
| 5,330,500 A | 7/1994 | Song |
| 5,330,768 A | 7/1994 | Park et al. |
| 5,342,348 A | 8/1994 | Kaplan |
| 5,342,395 A | 8/1994 | Jarrett et al. |
| 5,342,621 A | 8/1994 | Eury |
| 5,356,433 A | 10/1994 | Rowland et al. |
| 5,380,299 A | 1/1995 | Fearnot et al. |
| 5,383,925 A | 1/1995 | Schmitt |
| 5,385,580 A | 1/1995 | Schmitt |
| 5,389,106 A | 2/1995 | Tower |
| 5,399,666 A | 3/1995 | Ford |
| 5,417,981 A | 5/1995 | Endo et al. |
| 5,423,885 A | 6/1995 | Williams |
| 5,441,515 A | 8/1995 | Khosravi et al. |
| 5,443,458 A | 8/1995 | Eury et al. |
| 5,443,500 A | 8/1995 | Sigwart |
| 5,447,724 A | 9/1995 | Helmus et al. |
| 5,455,040 A | 10/1995 | Marchant |
| 5,462,990 A | 10/1995 | Hubbell et al. |
| 5,464,650 A | 11/1995 | Berg et al. |
| 5,502,158 A | 3/1996 | Sinclair et al. |
| 5,514,379 A | 5/1996 | Weissleder et al. |
| 5,527,337 A | 6/1996 | Stack et al. |
| 5,545,408 A | 8/1996 | Trigg et al. |
| 5,554,120 A | 9/1996 | Chen et al. |
| 5,556,413 A | 9/1996 | Lam |
| 5,569,463 A | 10/1996 | Helmus et al. |
| 5,578,046 A | 11/1996 | Liu et al. |
| 5,578,073 A | 11/1996 | Haimovich et al. |
| 5,591,199 A | 1/1997 | Porter et al. |
| 5,591,607 A | 1/1997 | Gryaznov et al. |
| 5,593,403 A | 1/1997 | Buscemi |
| 5,593,434 A | 1/1997 | Williams |
| 5,599,301 A | 2/1997 | Jacobs et al. |
| 5,599,922 A | 2/1997 | Gryaznov et al. |
| 5,605,696 A | 2/1997 | Eury et al. |
| 5,607,442 A | 3/1997 | Fischell et al. |
| 5,607,467 A | 3/1997 | Froix |
| 5,609,629 A | 3/1997 | Fearnot et al. |
| 5,618,299 A | 4/1997 | Khosravi et al. |
| 5,624,411 A | 4/1997 | Tuch |
| 5,628,730 A | 5/1997 | Shapland et al. |
| 5,629,077 A | 5/1997 | Turnlund et al. |
| 5,631,135 A | 5/1997 | Gryaznov et al. |
| 5,632,771 A | 5/1997 | Boatman et al. |
| 5,632,840 A | 5/1997 | Campbell |
| 5,637,113 A | 6/1997 | Tartaglia et al. |
| 5,649,977 A | 7/1997 | Campbell |
| 5,658,995 A | 8/1997 | Kohn et al. |
| 5,667,767 A | 9/1997 | Greff et al. |
| 5,667,796 A | 9/1997 | Otten |
| 5,670,558 A | 9/1997 | Onishi et al. |
| 5,679,400 A | 10/1997 | Tuch |
| 5,693,085 A | 12/1997 | Buirge et al. |
| 5,700,286 A | 12/1997 | Tartaglia et al. |
| 5,702,754 A | 12/1997 | Zhong |
| 5,707,385 A | 1/1998 | Williams |
| 5,711,763 A | 1/1998 | Nonami et al. |
| 5,716,981 A | 2/1998 | Hunter et al. |
| 5,725,549 A | 3/1998 | Lam |
| 5,726,297 A | 3/1998 | Gryaznov et al. |
| 5,728,751 A | 3/1998 | Patnaik |
| 5,733,326 A | 3/1998 | Tomonto et al. |
| 5,733,330 A | 3/1998 | Cox |
| 5,733,564 A | 3/1998 | Lehtinen |
| 5,733,925 A | 3/1998 | Kunz et al. |
| 5,735,897 A | 4/1998 | Buirge |
| 5,741,881 A | 4/1998 | Patnaik |
| 5,746,998 A | 5/1998 | Torchilin et al. |
| 5,756,457 A | 5/1998 | Wang et al. |
| 5,756,476 A | 5/1998 | Epstein et al. |
| 5,765,682 A | 6/1998 | Bley et al. |
| 5,766,204 A | 6/1998 | Porter et al. |
| 5,766,239 A | 6/1998 | Cox |
| 5,766,710 A | 6/1998 | Turnlund et al. |
| 5,769,883 A | 6/1998 | Buscemi et al. |
| 5,776,184 A | 7/1998 | Tuch |
| 5,780,807 A | 7/1998 | Saunders |
| 5,788,979 A | 8/1998 | Alt et al. |
| 5,800,392 A | 9/1998 | Racchini |
| 5,800,516 A | 9/1998 | Fine et al. |
| 5,811,447 A | 9/1998 | Kunz et al. |
| 5,820,917 A | 10/1998 | Tuch |
| 5,824,048 A | 10/1998 | Tuch |
| 5,824,049 A | 10/1998 | Ragheb et al. |
| 5,830,178 A | 11/1998 | Jones et al. |
| 5,830,461 A | 11/1998 | Billiar |
| 5,830,879 A | 11/1998 | Isner |
| 5,833,651 A | 11/1998 | Donovan et al. |
| 5,834,582 A | 11/1998 | Sinclair et al. |
| 5,836,962 A | 11/1998 | Gianotti |
| 5,837,008 A | 11/1998 | Berg et al. |
| 5,837,313 A | 11/1998 | Ding et al. |
| 5,837,835 A | 11/1998 | Gryaznov et al. |
| 5,840,083 A | 11/1998 | Braach-Maksvytis |
| 5,851,508 A | 12/1998 | Greff et al. |
| 5,853,408 A | 12/1998 | Muni |
| 5,854,207 A | 12/1998 | Lee et al. |
| 5,855,612 A | 1/1999 | Ohthuki et al. |
| 5,855,618 A | 1/1999 | Patnaik et al. |
| 5,858,746 A | 1/1999 | Hubbell et al. |
| 5,865,814 A | 2/1999 | Tuch |
| 5,868,781 A | 2/1999 | Killion |
| 5,869,127 A | 2/1999 | Zhong |
| 5,873,904 A | 2/1999 | Ragheb et al. |
| 5,874,101 A | 2/1999 | Zhong et al. |
| 5,874,109 A | 2/1999 | Ducheyne et al. |
| 5,874,165 A | 2/1999 | Drumheller |
| 5,876,433 A | 3/1999 | Lunn |
| 5,876,743 A | 3/1999 | Ibsen et al. |
| 5,877,224 A | 3/1999 | Brocchini et al. |
| 5,877,263 A | 3/1999 | Patnaik et al. |
| 5,879,713 A | 3/1999 | Roth et al. |
| 5,888,533 A | 3/1999 | Dunn |
| 5,891,192 A | 4/1999 | Murayama et al. |
| 5,897,955 A | 4/1999 | Drumheller |
| 5,906,759 A | 5/1999 | Richter |
| 5,914,182 A | 6/1999 | Drumheller |
| 5,916,870 A | 6/1999 | Lee et al. |
| 5,922,005 A | 7/1999 | Richter et al. |
| 5,925,720 A | 7/1999 | Kataoka et al. |
| 5,942,209 A | 8/1999 | Leavitt et al. |
| 5,948,428 A | 9/1999 | Lee et al. |
| 5,954,744 A | 9/1999 | Phan et al. |
| 5,955,509 A | 9/1999 | Webber et al. |
| 5,957,975 A | 9/1999 | Lafont et al. |
| 5,965,720 A | 10/1999 | Gryaznov et al. |
| 5,971,954 A | 10/1999 | Conway et al. |
| 5,976,182 A | 11/1999 | Cox |
| 5,980,564 A | 11/1999 | Stinson |
| 5,980,928 A | 11/1999 | Terry |
| 5,980,972 A | 11/1999 | Ding |
| 5,981,568 A | 11/1999 | Kunz et al. |
| 5,986,169 A | 11/1999 | Gjunter |

| | | | | | | |
|---|---|---|---|---|---|---|
| 5,997,468 | A | 12/1999 | Wolff et al. | 6,293,966 B1 | 9/2001 | Frantzen |
| 5,997,517 | A | 12/1999 | Whitbourne | 6,299,604 B1 | 10/2001 | Ragheb et al. |
| 6,010,445 | A | 1/2000 | Armini et al. | 6,303,901 B1 | 10/2001 | Perry et al. |
| 6,010,530 | A | 1/2000 | Goicoechea | 6,306,176 B1 | 10/2001 | Whitbourne |
| 6,015,541 | A | 1/2000 | Greff et al. | 6,312,459 B1 | 11/2001 | Huang et al. |
| 6,033,582 | A | 3/2000 | Lee et al. | 6,327,772 B1 | 12/2001 | Zadno-Azizi et al. |
| 6,042,875 | A | 3/2000 | Ding et al. | 6,331,313 B1 | 12/2001 | Wong et al. |
| 6,048,964 | A | 4/2000 | Lee et al. | 6,335,029 B1 | 1/2002 | Kamath et al. |
| 6,051,576 | A | 4/2000 | Ashton et al. | 6,346,110 B2 | 2/2002 | Wu |
| 6,051,648 | A | 4/2000 | Rhee et al. | 6,358,556 B1 * | 3/2002 | Ding et al. ............... 427/2.24 |
| 6,056,993 | A | 5/2000 | Leidner et al. | 6,375,826 B1 | 4/2002 | Wang et al. |
| 6,060,451 | A | 5/2000 | DiMaio et al. | 6,379,381 B1 | 4/2002 | Hossainy et al. |
| 6,060,518 | A | 5/2000 | Kabanov et al. | 6,387,121 B1 | 5/2002 | Alt |
| 6,066,156 | A | 5/2000 | Yan | 6,387,124 B1 | 5/2002 | Buscemi et al. |
| 6,071,266 | A | 6/2000 | Kelley | 6,388,043 B1 | 5/2002 | Langer et al. |
| 6,074,659 | A | 6/2000 | Kunz et al. | 6,395,326 B1 | 5/2002 | Castro et al. |
| 6,080,177 | A | 6/2000 | Igaki et al. | 6,409,761 B1 | 6/2002 | Jang |
| 6,080,488 | A | 6/2000 | Hostettler et al. | 6,419,692 B1 | 7/2002 | Yang et al. |
| 6,083,258 | A | 7/2000 | Yadav | 6,423,092 B2 | 7/2002 | Datta et al. |
| 6,093,463 | A | 7/2000 | Thakrar | 6,451,373 B1 | 9/2002 | Hossainy et al. |
| 6,096,070 | A | 8/2000 | Ragheb et al. | 6,461,632 B1 | 10/2002 | Gogolewski |
| 6,096,525 | A | 8/2000 | Patnaik | 6,464,720 B2 | 10/2002 | Boatman et al. |
| 6,099,562 | A * | 8/2000 | Ding et al. ............... 623/1.46 | 6,479,565 B1 | 11/2002 | Stanley |
| 6,103,230 | A | 8/2000 | Billiar et al. | 6,485,512 B1 | 11/2002 | Cheng |
| 6,107,416 | A | 8/2000 | Patnaik et al. | 6,492,615 B1 | 12/2002 | Flanagan |
| 6,110,188 | A | 8/2000 | Narciso, Jr. | 6,494,862 B1 | 12/2002 | Ray et al. |
| 6,110,483 | A | 8/2000 | Whitbourne et al. | 6,494,908 B1 | 12/2002 | Huxel et al. |
| 6,113,629 | A | 9/2000 | Ken | 6,495,156 B2 | 12/2002 | Wenz et al. |
| 6,117,979 | A | 9/2000 | Hendriks et al. | 6,503,556 B2 | 1/2003 | Harish et al. |
| 6,120,536 | A | 9/2000 | Ding et al. | 6,503,954 B1 | 1/2003 | Bhat et al. |
| 6,120,904 | A | 9/2000 | Hostettler et al. | 6,506,437 B1 | 1/2003 | Harish et al. |
| 6,121,027 | A | 9/2000 | Clapper et al. | 6,511,748 B1 | 1/2003 | Barrows |
| 6,125,523 | A | 10/2000 | Brown et al. | 6,517,888 B1 | 2/2003 | Weber |
| 6,127,173 | A | 10/2000 | Eckstein et al. | 6,527,801 B1 | 3/2003 | Dutta |
| 6,129,761 | A | 10/2000 | Hubbell | 6,527,863 B1 | 3/2003 | Pacetti et al. |
| 6,129,928 | A | 10/2000 | Sarangapani et al. | 6,534,112 B1 * | 3/2003 | Bouchier et al. ........... 427/2.24 |
| 6,150,630 | A | 11/2000 | Perry et al. | 6,537,589 B1 | 3/2003 | Chae et al. |
| 6,153,252 | A | 11/2000 | Hossainy et al. | 6,539,607 B1 | 4/2003 | Fehring et al. |
| 6,159,951 | A | 12/2000 | Karpeisky et al. | 6,540,776 B2 | 4/2003 | Sanders Millare et al. |
| 6,160,084 | A | 12/2000 | Langer et al. | 6,540,777 B2 | 4/2003 | Stenzel |
| 6,165,212 | A | 12/2000 | Dereume et al. | 6,544,223 B1 | 4/2003 | Kokish |
| 6,166,130 | A | 12/2000 | Rhee et al. | 6,544,543 B1 | 4/2003 | Mandrusov et al. |
| 6,169,170 | B1 | 1/2001 | Gryaznov et al. | 6,544,582 B1 | 4/2003 | Yoe |
| 6,171,609 | B1 | 1/2001 | Kunz | 6,554,854 B1 | 4/2003 | Flanagan |
| 6,174,330 | B1 | 1/2001 | Stinson | 6,555,157 B1 | 4/2003 | Hossainy |
| 6,177,523 | B1 | 1/2001 | Reich et al. | 6,558,733 B1 | 5/2003 | Hossainy et al. |
| 6,183,505 | B1 | 2/2001 | Mohn, Jr. et al. | 6,565,599 B1 | 5/2003 | Hong et al. |
| 6,187,045 | B1 | 2/2001 | Fehring et al. | 6,565,659 B1 | 5/2003 | Pacetti et al. |
| 6,203,551 | B1 | 3/2001 | Wu | 6,569,191 B1 | 5/2003 | Hogan |
| 6,210,715 | B1 | 4/2001 | Starling et al. | 6,569,193 B1 | 5/2003 | Cox et al. |
| 6,214,901 | B1 | 4/2001 | Chudzik et al. | 6,572,644 B1 | 6/2003 | Moein |
| 6,224,626 | B1 | 5/2001 | Steinke | 6,572,672 B2 | 6/2003 | Yadav et al. |
| 6,228,845 | B1 | 5/2001 | Donovan et al. | 6,574,851 B1 | 6/2003 | Mirizzi |
| 6,231,600 | B1 | 5/2001 | Zhong | 6,585,755 B2 | 7/2003 | Jackson et al. |
| 6,240,616 | B1 | 6/2001 | Yan | 6,585,765 B1 | 7/2003 | Hossainy et al. |
| 6,245,076 | B1 | 6/2001 | Yan | 6,585,926 B1 | 7/2003 | Mirzaee |
| 6,245,103 | B1 | 6/2001 | Stinson | 6,592,614 B2 | 7/2003 | Lenker et al. |
| 6,245,753 | B1 | 6/2001 | Byun et al. | 6,592,617 B2 | 7/2003 | Thompson |
| 6,248,344 | B1 | 6/2001 | Ylanen et al. | 6,605,154 B1 | 8/2003 | Villareal |
| 6,251,135 | B1 | 6/2001 | Stinson et al. | 6,613,072 B2 | 9/2003 | Lau et al. |
| 6,251,136 | B1 | 6/2001 | Guruwaiya et al. | 6,626,939 B1 | 9/2003 | Burnside et al. |
| 6,251,142 | B1 | 6/2001 | Bernacca et al. | 6,635,269 B1 | 10/2003 | Jennissen |
| 6,254,632 | B1 | 7/2001 | Wu et al. | 6,645,243 B2 | 11/2003 | Vallana et al. |
| 6,258,121 | B1 | 7/2001 | Yang et al. | 6,656,162 B2 | 12/2003 | Santini, Jr. et al. |
| 6,273,913 | B1 | 8/2001 | Wright et al. | 6,664,335 B2 | 12/2003 | Krishnan |
| 6,281,262 | B1 | 8/2001 | Shikinami | 6,666,214 B2 | 12/2003 | Canham |
| 6,283,947 | B1 | 9/2001 | Mirzaee | 6,667,049 B2 | 12/2003 | Janas et al. |
| 6,283,949 | B1 | 9/2001 | Roorda | 6,669,723 B2 | 12/2003 | Killion et al. |
| 6,284,305 | B1 | 9/2001 | Ding et al. | 6,669,980 B2 * | 12/2003 | Hansen ............... 427/2.24 |
| 6,284,333 | B1 | 9/2001 | Wang et al. | 6,676,697 B1 | 1/2004 | Richter |
| 6,287,332 | B1 | 9/2001 | Bolz et al. | 6,679,980 B1 | 1/2004 | Andreacchi |
| 6,287,628 | B1 | 9/2001 | Hossainy et al. | 6,689,375 B2 | 2/2004 | Wahlig et al. |
| 6,290,721 | B1 | 9/2001 | Heath | 6,695,920 B1 | 2/2004 | Pacetti et al. |

| | | | | | | |
|---|---|---|---|---|---|---|
| 6,706,273 | B1 | 3/2004 | Roessler | EP | 0 910 584 | 4/1999 |
| 6,709,379 | B1 | 3/2004 | Brandau et al. | EP | 0 923 953 | 6/1999 |
| 6,719,934 | B2 | 4/2004 | Stinson | EP | 0 953 320 | 11/1999 |
| 6,719,989 | B1 | 4/2004 | Matsushima et al. | EP | 0 970 711 | 1/2000 |
| 6,720,402 | B2 | 4/2004 | Langer et al. | EP | 0 982 041 | 3/2000 |
| 6,746,773 | B2 | 6/2004 | Llanos et al. | EP | 1 273 314 | 1/2003 |
| 6,752,826 | B2 | 6/2004 | Holloway et al. | GB | 2 247 696 | 3/1992 |
| 6,753,007 | B2 | 6/2004 | Haggard et al. | JP | 2001-190687 | 7/2001 |
| 6,764,505 | B1 | 7/2004 | Hossainy et al. | WO | WO89/03232 | 4/1989 |
| 6,818,063 | B1 | 11/2004 | Kerrigan | WO | WO90/01969 | 3/1990 |
| 6,846,323 | B2 | 1/2005 | Yip et al. | WO | WO90/04982 | 5/1990 |
| 2001/0018469 | A1 | 8/2001 | Chen et al. | WO | WO90/06094 | 6/1990 |
| 2001/0037145 | A1 | 11/2001 | Guruwaiya et al. | WO | WO91/12846 | 9/1991 |
| 2001/0044652 | A1 | 11/2001 | Moore | WO | WO91/17744 | 11/1991 |
| 2002/0002399 | A1 | 1/2002 | Huxel et al. | WO | WO91/17789 | 11/1991 |
| 2002/0004060 | A1 | 1/2002 | Heublein et al. | WO | WO92/10218 | 6/1992 |
| 2002/0004101 | A1 | 1/2002 | Ding et al. | WO | WO93/06792 | 4/1993 |
| 2002/0062148 | A1 | 5/2002 | Hart | WO | WO94/21196 | 9/1994 |
| 2002/0065553 | A1 | 5/2002 | Weber | WO | WO95/10989 | 4/1995 |
| 2002/0077693 | A1 | 6/2002 | Barclay et al. | WO | WO95/29647 | 11/1995 |
| 2002/0091433 | A1 | 7/2002 | Ding et al. | WO | WO96/40174 | 12/1996 |
| 2002/0111590 | A1 | 8/2002 | Davila et al. | WO | WO97/10011 | 3/1997 |
| 2002/0116050 | A1 | 8/2002 | Kocur | WO | WO97/45105 | 12/1997 |
| 2002/0138133 | A1 | 9/2002 | Lenz et al. | WO | WO97/46590 | 12/1997 |
| 2002/0155212 | A1 | 10/2002 | Hossainy | WO | WO98/04415 | 2/1998 |
| 2002/0161114 | A1 | 10/2002 | Gunatillake et al. | WO | WO98/17331 | 4/1998 |
| 2003/0033001 | A1 | 2/2003 | Igaki | WO | WO98/36784 | 8/1998 |
| 2003/0065377 | A1 | 4/2003 | Davila et al. | WO | WO99/01118 | 1/1999 |
| 2003/0093107 | A1 | 5/2003 | Parsonage et al. | WO | WO99/03515 | 1/1999 |
| 2003/0099712 | A1 | 5/2003 | Jayaraman | WO | WO99/16386 | 4/1999 |
| 2003/0100865 | A1 | 5/2003 | Santini, Jr. et al. | WO | WO99/38546 | 8/1999 |
| 2003/0105518 | A1 | 6/2003 | Dutta | WO | WO99/42147 | 8/1999 |
| 2003/0105530 | A1 | 6/2003 | Pirhonen | WO | WO99/63981 | 12/1999 |
| 2003/0171053 | A1 | 9/2003 | Sanders | WO | WO 00/02599 | 1/2000 |
| 2003/0187495 | A1 | 10/2003 | Cully et al. | WO | WO 00/12147 | 3/2000 |
| 2003/0208259 | A1 | 11/2003 | Penhasi | WO | WO 00/18446 | 4/2000 |
| 2003/0209835 | A1 | 11/2003 | Chun et al. | WO | WO 00/32238 | 6/2000 |
| 2003/0226833 | A1 | 12/2003 | Shapovalov et al. | WO | WO 00/64506 | 11/2000 |
| 2003/0236565 | A1 | 12/2003 | Fifer | WO | WO 01/01890 | 1/2001 |
| 2004/0093077 | A1 | 5/2004 | White et al. | WO | WO 01/15751 | 3/2001 |
| 2004/0098095 | A1 | 5/2004 | Burnside et al. | WO | WO 01/17577 | 3/2001 |
| 2004/0111149 | A1 | 6/2004 | Stinson | WO | WO 01/45763 | 6/2001 |
| 2004/0127970 | A1 | 7/2004 | Weber | WO | WO 01/49338 | 7/2001 |
| 2004/0143317 | A1 | 7/2004 | Stinson et al. | WO | WO 01/74414 | 10/2001 |
| 2004/0167610 | A1 | 8/2004 | Fleming, III | WO | WO 02/003890 | 1/2002 |
| 2004/0220665 | A1* | 11/2004 | Hossainy et al. ......... 623/1.42 | WO | WO 02/026162 | 4/2002 |
| 2004/0258728 | A1* | 12/2004 | Nchekwube et al. ....... 424/423 | WO | WO 02/34311 | 5/2002 |
| | | | | WO | WO 02/056790 | 7/2002 |
| | | FOREIGN PATENT DOCUMENTS | | WO | WO 03/000308 | 1/2003 |
| DE | | 197 31 021 | 1/1999 | WO | WO 03/022323 * | 3/2003 |
| DE | | 198 56 983 | 12/1999 | WO | WO 03/028780 | 4/2003 |
| EP | | 0 108 171 | 5/1984 | WO | WO 03/037223 | 5/2003 |
| EP | | 0 144 534 | 6/1985 | WO | WO 03/039612 | 5/2003 |
| EP | | 0 301 856 | 2/1989 | WO | WO 2004/023985 | 3/2004 |
| EP | | 0 364 787 | 4/1990 | | | |
| EP | | 0 397 500 | 11/1990 | | | |
| EP | | 0 464 755 | 1/1992 | | | |
| EP | | 0 493 788 | 7/1992 | | | |
| EP | | 0 514 406 | 11/1992 | | | |
| EP | | 0 554 082 | 8/1993 | | | |
| EP | | 0 578 998 | 1/1994 | | | |
| EP | | 0 604 022 | 6/1994 | | | |
| EP | | 0 621 017 | 10/1994 | | | |
| EP | | 0 623 354 | 11/1994 | | | |
| EP | | 0 665 023 | 8/1995 | | | |
| EP | | 0 701 802 | 3/1996 | | | |
| EP | | 0 709 068 | 5/1996 | | | |
| EP | | 0 716 836 | 6/1996 | | | |
| EP | | 0 809 999 | 12/1997 | | | |
| EP | | 0 832 655 | 4/1998 | | | |
| EP | | 0 850 651 | 7/1998 | | | |
| EP | | 0 879 595 | 11/1998 | | | |

OTHER PUBLICATIONS

Aoyagi et al., *Preparation of cross-linked aliphatic polyester and application to thermo-responsive material*, Journal of Controlled Release 32:87-96 (1994).

Baird et al., *Dielectric behaviour and morphology of polyvinylidene fluoride*, Journal of Material Science 10:1248-1251 (1975).

Barath et al., *Low Dose of Antitumor Agents Prevents Smooth Muscle Cell Proliferation After Endothelial Injury*, JACC 13(2): 252A (Abstract) (Feb. 1989).

Barbucci et al., *Coating of commercially available materials with a new heparinizable material*, J. Biomed. Mater. Res. 25:1259-1274 (Oct. 1991).

Black et al., *Glass Transitions of Some Block Copolymers*, Journal of Applied Polymer Science 18:2307-2310 (1974).

Bliznyuk et al., *Surface Glass Transition Temperature of Amorphous Polystyrene Measured By SFM*, p. 1-5, no date.

Buchholz et al., *Cooling rate dependance of the glass transition temperature of polymer melts: Molecular dynamics study*, Journal of Chemical Physics 117(15):7364-7372 (Oct. 15, 2002).

Chung et al., *Inner core segment design for drug delivery control of thermo-responsive polymeric micelles*, Journal of Controlled Release 65:93-103 (2000).

Dev et al., *Kinetics of Drug Delivery to the Arterial Wall Via Polyurethane-Coated Removable Nitinol Stent: Comparative Study of Two Drugs*, Catheterization and Cardiovascular Diagnosis 34:272-278 (1995).

Dichek et al., *Seeding of Intravascular Stents with Genetically Engineered Endothelial Cells*, Circ. 80(5):1347-1353 (Nov. 1989).

Ding et al., *Novel Synthesis of Poly(p-phenylene sulfide) from Cyclic Disulfide Oligomers*, Macromolecules 29:4811-4812 (1996).

Eigler et al., *Local Arterial Wall Drug Delivery from a Polymer Coated Removable Metallic Stent: Kinetics, Distribution, and Bioactivity of Forskolin*, JACC, 4A (701-1), Abstract (Feb. 1994), no page numbers.

Fernandez-Martin et al., *Glass Transition Temperature and Heat Capacity of Heterotacticlike PMMA*, Journal of Polymer Science: Polymer Physics Edition 19:1353-1363 (1981).

Forrest et al., *Effect of Free Surfaces on the Glass Transistion Temperature of Thin Polymer Films*, Physical Review Letters 77(10):2002-2005 (Sep. 2, 1996).

Fryer et al., *Dependence of the Glass Transition Temperature of Polymer Films on Interfacial Energy and Thickness*, Macromolecules 34(16):5627-5634 (2001).

Fujii et al., *Investigation of the Stereoregularity of Poly(vinyl Alcohol)*, Journal of Polymer Science: Part A 2:2327-2347 (1964).

Gee et al., *The effect of ionizing radiation on the thermal properties of linear high polymers: Part 2. Nylon-6*, pp. 192-197 (1970).

Grohens et al., *Tacticity and surface chemistry effects on the glass transission temperature of thin supported PMMA films*, Mat. Res. Soc. Symp. 629:FF1.7.1-FF1.7.7 (2000).

Helmus, *Overview of Biomedical Materials*, MRS Bulletin, pp. 33-38 (Sep. 1991).

Herdeg et al., *Antiproliferative Stent Coatings: Taxol and Related Compounds*, Semin. Intervent. Cardiol. 3:197-199 (1998).

Inoue et al., *An AB block copolymer of oligo(methyl methacrylate) and poly(acrylic acid) for micellar delivery of hydrophobic drugs*, Journal of Controlled Release 51:221-229 (1998).

Kataoka et al., *Block copolymer micelles as vehicles for drug delivery*, Journal of Controlled Release 24:119-132 (1993).

Levy et al., *Strategies For Treating Arterial Restenosis Using Polymeric Controlled Release Implants*, Biotechnol. Bioact. Polym. [Proc. Am. Chem. Soc. Symp.], pp. 259-268 (1994).

Löfgren et al., *Synthesis and Characterization of Biodegradable Homopolymers and Block Copolymers Based on 1,5-Dioxepan-2-one*, Macromolecules 27:5556-5562 (1994).

Liu et al., *Drug release characteristics of unimolecular polymeric micelles*, Journal of Controlled Release 68:167-174 (2000).

Lotz, *Phase Transitions and Structure of Crystalline Polymers*, pp. 1-27, no date.

Marconi et al., *Covalent bonding of heparin to a vinyl copolymer for biomedical applications*, Biomaterials 18(12):885-890 (1997).

Matsumaru et al., *Embolic Materials For Endovascular Treatment of Cerebral Lesions*, J. Biomater. Sci. Polymer Edn 8(7):555-569 (1997).

Micoulaut et al., *Glass Transition temperature variation, crosslinking and structure in network glasses: A stochastic approach*, Europhysics Letters 47(5):568-574 (Sep. 1, 1999).

Miyazaki et al., *Antitumor Effect of Implanted Ethylene-Vinyl Alcohol Copolymer Matrices Containing Anticancer Agents on Ehrlich Ascites Carcinoma and P388 Leukemia in Mice*, Chem. Pharm. Bull. 33(6) 2490-2498 (1985).

Miyazawa et al., *Effects of Pemirolast and Tranilast on Intimal Thickening After Arterial Injury in the Rat*, J. Cardiovasc. Pharmacol., pp. 157-162 (1997).

Nordrehaug et al., *A novel biocompatible coating applied to coronary stents*, European Heart Journal 14, p. 321 (P1694), Abstr. Suppl. (1993).

Ohsawa et al., *Preventive Effects of an Antiallergic Drug, Pemirolast Potassium, on Restenosis After Percutaneous Transluminal Coronary Angioplasty*, American Heart Journal 136(6):1081-1087 (Dec. 1998).

Ozaki et al., *New Stent Technologies*, Progress in Cardiovascular Diseases, vol. XXXIX(2):129-140 (Sep./Oct. 1996).

Parravicini et al., *Crystallization of Poly(Ethylene Terephthalate) (PET) from the Oriented Mesomorphic Form*, pp. 875-885 (1994).

Pechar et al., *Poly(ethylene glycol) Multiblock Copolymers as a Carrier of Anti-Cancer Drug Doxorubicin*, Bioconjugate Chemistry 11(2):131-139 (Mar./Apr. 2000).

Peng et al., *Role of polymers in improving the results of stenting in coronary arteries*, Biomaterials 17:685-694 (1996).

Rogers et al., *Glass Formation in Polymers. I. The Glass Transitions of the Poly-(n-Alkyl Methacrylates)*, 61:985-990 (Jul. 1957).

Scott et al., *Ethylene-Vinyl Acetate Semi-Batch Emulsion Copolymerization: Use of Factorial Experiments for Process Optimization*, pp. 539-555 (1993).

Shigeno, *Prevention of Cerebrovascular Spasm By Bosentan, Novel Endothelin Receptor*, Chemical Abstract 125:212307 (1996).

Sichima, *Characterization of Polymers by TMA*, Perkin Elmer Polymers technical note (9 pages), no date.

Sun et al., *Novel Copolyesters Containing Naphthalene Structure. I. Form Bis(hydroxyalkl)naphthalate and Bis[4-(2-hydroxyethoxy)aryl] Compounds*, Journal of Polymer Science: Part A: Polymer Chemistry 34:1783-1792 (1996).

Taylor et al., *Applied approach to film formation; The glass transition temperature evolution of plasticized latex films* (22 pages), no date.

Tsige et al., *Stimulation of the glass transition temperature in poly(methyl methacrylate)*, Physical Review E 65:021805-1-021805-8 (2002).

van Beusekom et al., *Coronary stent coatings*, Coronary Artery Disease 5(7):590-596 (Jul. 1994).

Wilensky et al., *Methods and Devices for Local Drug Delivery in Coronary and Peripheral Arteries*, Trends Cardiovasc. Med. 3(5):163-170 (1993).

Yokoyama et al., *Characterization of physical entrapment and chemical conjugation of adriamycin in polymeric micelles and their design for in vivo delivery to a solid tumor*, Journal of Controlled Release 50:79-92 (1998).

U.S. Appl. No. 10/317,435, filed Dec. 11, 2002, Hossainy et al.

Anonymous, *Bioabsorbable stent mounted on a catheter having optical coherence tomography capabilities*, Research Disclosure, Sep. 2004, pp. 1159-1162.

Ansari, *Tubal Reanastomosis Using Absorbable Stent*, International Journal of Fertility, vol. 23, No. 4, pp. 242-243 (1978).

Ansari, *End-to-end tubal anastomosis using an absorbable stent*, Fertility and Sterility, vol. 32(2), pp. 197-201 (Aug. 1979).

Bull, *Parylene Coating for Medical Applications*, Medical Product Manufacturing News 1 pg. (Mar. 1993).

Casper et al., *Fiber-Reinforced Absorbable Composite for Orthopedic Surgery*, Polymeric Materials Science and Engineering, 53: pp. 497-501 (1985).

Detweiler et al., *Sutureless Anastomosis of the Small Intestine and the Colon in Pigs Using an Absorbable Intraluminal Stent and Fibrin Glue*, Journal of Investigative Surgery, vol. 8(2), pp. 129-140 (Mar. 1995).

Detweiler et al., *Sutureless Cholecystojejunostomy in Pigs Using an Absorbable Intraluminal Stent and Fibrin Glue*, Journal of Investigative Surgery, vol. 9(1), pp. 13-26 (Jan./Feb. 1996).

Detweiler et al., *Sliding, Absorbable, Reinforced Ring and an Axially Driven Stent Placement Device for Sutureless Fibrin Glue Gastrointestinal Anastomisis*, Journal of Investigative Surgery, vol. 9(6), pp. 495-504 (Nov./Dec. 1996).

Detweiler et al., *Gastrointestinal Sutureless Anastomosis Using Fibrin Glue: Reinforcement of the Sliding Absorbable Intraluminal Nontoxic Stent and Development of a Stent Placement Device*, Journal of Investigative Surgery, vol. 9(2), pp. 111-130 (Mar./Apr. 1996).

Devanathan et al., *Polymeric Conformal Coatings for Implantable Electronic Devices*, IEEE Transactions on Biomedical Engineering, vol. BME-27(11), pp. 671-675 (1980).

Elbert et al., *Conjugate Addition Reactions Combined with Free-Radical Cross-Linking for the Design of Materials for Tissue Engineering*, Biomacromolecules 2, pp. 430-441 (2001).

Feng-Chun et al., *Assessment of Tissue Blood Flow Following Small Artery Welding with an Intraluminal Dissolvable Stent*, Microsurgery, vol. 19(3), 148-152 (1999).

Hahn et al., *Glow Discharge Polymers as Coatings for Implanted Devices*, ISA, pp. 109-111 (1981).

Hahn et al., *Biocompatibility of Glow-Discharge-Polymerized Films and Vacuum-Deposited Parylene*, J. Applied Polymer Sci, 38, pp. 55-64 (1984).

Kelley et al., *Totally Resorbable High-Strength Composite Material*, Advances in Biomedical Polymers, 35, pp. 75-85 (1987).

Kubies et al., *Microdomain Structure In polyactide-block-poly(ethylene oxide) copolymers films*, Biomaterials 21, pp. 529-536 (2000).

Kutryk et al., *Coronary Stenting: Current Perspectives*, a companion to the Handbook of Coronary Stents 16 pgs. (1999).

Mauduit et al., *Hydrolytic degradation of films prepared from blends of high and low molecular weight poly(DL-lactic acid)s*, J. Biomed. Mater. Res. v. 30, pp. 201-207 (1996).

Martin et al., *Enhancing the biological activity of immobilized osteopontin using a type-1 collagen affinity coating*, J. Biomed. Mater Res 70A, pp. 10-19 (2004).

Middleton et al., *Synthetic biodegradable polymers as orthopedic devices*, Biomaterials, vol. 21, pp. 2335-2346 (2000).

Muller et al., *Advances in Coronary Angioplasty: Endovascular Stents*, Coron. Arter. Dis., 1(4), pp. 438-448 (Jul./Aug. 1990).

Nichols et al., *Electrical Insulation of Implantable Devices by Composite Polymer Coatings*, ISA Transactions, 26(4), pp. 15-18 (1987).

Peuster et al., *A novel approach to temporary stenting: degradable cardiovascular stents produced from corrodible metal-results 6-18 months after implantation into New Zealand white rabbits*, Heart 86, pp. 563-569 (2001).

Pietrzak et al., *Bioresorbable implants—practical considerations*, Bone v. 19, No. 1, Supplement Jul. 1996: 109S-119S.

Pietrzak et al., *Bioabsorbable Fixation Devices: Status for the Craniomaxillofacial Surgeon*, J. Craniofaxial Surg. 2, pp. 92-96 (1997).

von Recum et al., *Degradation of polydispersed poly(L-lactic acid) to modulate lactic acid release*, Biomaterials 16, pp. 441-445 (1995).

Redman, *Clinical Experience with Vasovasostomy Utilizing Absorbable Intravasal Stent*, Urology, vol. 20(1), pp. 59-61 (Jul. 1982).

Rust et al., *The Effect of Absorbable Stenting on Postoperative Stenosis of the Surgically Enlarged Maxillary Sinus Ostia in a Rabbit Animal Model*, Archives of Otolaryngology, vol. 122(12) pp. 1395-1397 (Dec. 1996).

Schatz, *A View of Vascular Stents*, Circulation, 79(2), pp. 445-457 (Feb. 1989).

Schmidt et al., *Long-Term Implants of Parylene-C Coated Microelectrodes*, Med & Biol Eng & Comp, 26(1), pp. 96-101 (Jan. 1988).

Spagnuolo et al., *Gas 1 is induced by VE-cadherin and vascular endothelial growth factor and inhibits endothelial cell apoptosis*, Blood 103, pp. 3005-3012 (2004).

Tamai et al., *Initial and 6-Month Results of Biodegradable Poly-I-Lactic Acid Coronary Stents in Humans*, Circulation , pp. 399-404 (2000).

Tsui et al., *Biodegradable Polymeric Stents*, Current Interventional Cardiology Reports 3, pp. 10-17 (2001).

Völkel et al., *Targeting of immunoliposomes to endothelial cells using a single -chain Fv fragment directed against human endoglin (CD105)*, Biochemica et Biophysica Acta 1663, pp. 158-166 (2004).

Yau et al. Modern Size-Exclusion Liquid Chromatography, Wiley-Interscience Publication, (1979).

* cited by examiner

FLUID TREATMENT OF A POLYMERIC COATING ON AN IMPLANTABLE MEDICAL DEVICE

BACKGROUND OF THE INVENTION

1. Field of the Invention

The invention relates to implantable medical devices, one example of which is a stent. More particularly, the invention relates to a method of coating such implantable medical devices.

2. Description of the Background

Percutaneous transluminal coronary angioplasty (PTCA) is a procedure for treating heart disease. A catheter assembly having a balloon portion is introduced percutaneously into the cardiovascular system of a patient via the brachial or femoral artery. The catheter assembly is advanced through the coronary vasculature until the balloon portion is positioned across the occlusive lesion. Once in position across the lesion, the balloon is inflated to a predetermined size to remodel the vessel wall. The balloon is then deflated to a smaller profile to allow the catheter to be withdrawn from the patient's vasculature.

A problem associated with the above procedure includes formation of intimal flaps or torn arterial linings, which can collapse and occlude the conduit after the balloon is deflated. Vasospasms and recoil of the vessel wall also threaten vessel closure. Moreover, thrombosis and restenosis of the artery may develop over several months after the procedure, which may necessitate another procedure or a surgical by-pass operation. To reduce the partial or total occlusion of the artery by the collapse of arterial lining and to reduce the chance of the development of thrombosis and restenosis a stent is implanted in the lumen to maintain the vascular patency.

Stents act as scaffoldings, functioning to physically hold open and, if desired, to expand the wall of the passageway. Typically, stents are capable of being compressed so that they can be inserted through small lumens via catheters and then expanded to a larger diameter once they are at the desired location. Mechanical intervention via stents has reduced the rate of restenosis as compared to balloon angioplasty. Yet, restenosis is still a significant clinical problem with rates ranging from 20-40%. When restenosis does occur in the stented segment, its treatment can be challenging, as clinical options are more limited as compared to lesions that were treated solely with a balloon.

Stents are used not only for mechanical intervention but also as vehicles for providing biological therapy. Biological therapy can be achieved by medicating the stents. Medicated stents provide for the local administration of a therapeutic substance at the diseased site. In order to provide an efficacious concentration to the treated site, systemic administration of such medication often produces adverse or even toxic side effects for the patient. Local delivery is a preferred method of treatment in that smaller total levels of medication are administered in comparison to systemic dosages, but are concentrated at a specific site. Local delivery thus produces fewer side effects and achieves more favorable results.

One proposed method of medicating stents involves the use of a polymeric carrier coated onto the surface of the stent. A composition including a solvent, a polymer dissolved in the solvent, and an active agent dispersed in the blend is applied to the stent by immersing the stent in the composition or by spraying the composition onto the stent. The solvent is allowed to evaporate, leaving on the stent strut surfaces a coating of the polymer and the active agent impregnated in the polymer.

A potential shortcoming of the foregoing method of medicating stents is that the release rate of the active agent may be too high to provide an efficacious treatment. This shortcoming may be especially pronounced with certain active agents. For instance, it has been found that the release rate of 40-O-(2-hydroxy)ethyl-rapamycin from a standard polymeric coating is greater than 50% in about 24 hours. Thus, there is a need for a coating that reduces the release rate of active agents in order to provide a more efficacious release rate profile.

Another shortcoming of the foregoing method of medicating stents is that there can be significant manufacturing inconsistencies. For instance, there can be release rate variability among different stents. It is believed that when some polymers dry on a stent surface to form a coating, different polymer morphologies can develop for different stent coatings, even if the coating process parameters are consistent. The differences in polymer morphology may cause the release rate of the active agent from the polymeric coatings to vary significantly. As a consequence of the inconsistent release rate profiles among stents, there can be clinical complications. Additionally, when stents are stored, the release rate from the stent coating can change during the storage time, known as "release rate drift." Thus, there is a need for a method that reduces the variability of the release rate of active agents among stents and over time. The present invention provides a method and coating to meet the foregoing as well as other needs.

SUMMARY

In accordance with one aspect of the invention, a method of manufacturing an implantable medical device is disclosed including applying a composition to an implantable medical device, the composition including a polymer, an active agent and a solvent; allowing the solvent to evaporate to form a dry coating, the dry coating comprising less than about 2% residual fluid content (w/w); applying a fluid to the dry coating, the fluid being substantially free from any polymer; and allowing the fluid to evaporate from the coating. In one embodiment, the fluid is substantially free from any active agents. In another embodiment, applying the fluid includes spraying the fluid onto the coating or immersing the device into a bath of fluid. In a further embodiment, the temperature of the fluid is equal to or greater than the glass transition temperature of the polymer.

In accordance with a further aspect of the present invention, a method of manufacturing a stent coating is disclosed including applying a composition to a stent, the composition including a semicrystalline polymer and a solvent; allowing the solvent to evaporate to form a dry coating, the dry coating comprising less than about 2% residual fluid content (w/w); and exposing the coating to a fluid for a sufficient duration to increase the crystallinity of the polymer in at least a portion of the coating, the fluid being substantially free from any polymer. In one embodiment, the polymer comprises an ethylene vinyl alcohol copolymer or poly (vinylidene fluoride-co-hexafluoropropene). In another embodiment, exposing the coating to a fluid includes immersing the stent into a bath of fluid. In yet another embodiment, the stent is immersed for about 30 minutes to about twelve hours.

DETAILED DESCRIPTION

Coating

Herein is disclosed a method of manufacturing a drug eluting implantable device, such as a stent, by using a fluid treatment process. The method includes applying a fluid to a dry polymeric coating. The coating can include one or more active agents dispersed within one or more polymers. The active agent can be any substance capable of exerting a therapeutic or prophylactic effect. "Polymer," "poly," and "polymeric" are inclusive of homopolymers, copolymers, terpolymers etc., including random, alternating, block, cross-linked, blends and graft variations thereof.

Some of embodiments of the polymeric coating are illustrated by FIGS. 1A-1E. The Figures have not been drawn to scale, and the thickness of the various layers have been over or under emphasized for illustrative purposes.

Figure 1A:
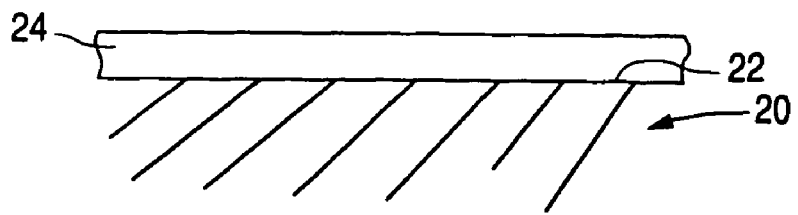
FIGS. 1A-1E illustrate coatings deposited over an implantable medical substrate in accordance with various embodiments of the present invention.

Referring to FIG. 1A, a body of a medical substrate 20, such as a stent, is illustrated having a surface 22. A reservoir layer 24 having a polymer and an active agent (e.g., 40-O-(2-hydroxy)ethyl-rapamycin) dispersed in the polymer is deposited on surface 22. The polymer in reservoir layer 24 can be a homopolymer, copolymer, terpolymer, etc. and can include random, alternating, block, cross-linked, blends and graft variations thereof. Reservoir layer 24 can release the active agent when medical substrate 20 is inserted into a biological lumen.

Figure 1B:
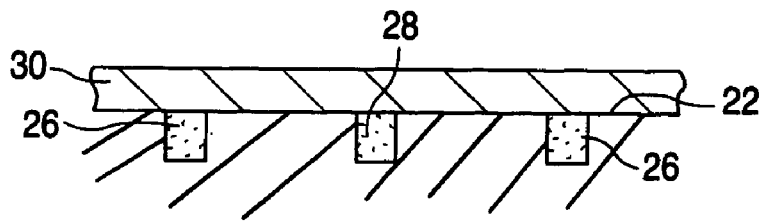

Referring to FIG. 1B, medical substrate 20 includes cavities or micro-pores 26 formed in the body for releasably containing an active agent, as illustrated by dotted region 28. A barrier layer or rate-reducing membrane 30 including a polymer is disposed on surface 22 of medical substrate 20, covering cavities 26. Barrier layer 30 functions to reduce the rate of release of an active agent from medical substrate 20.

Figure 1C:
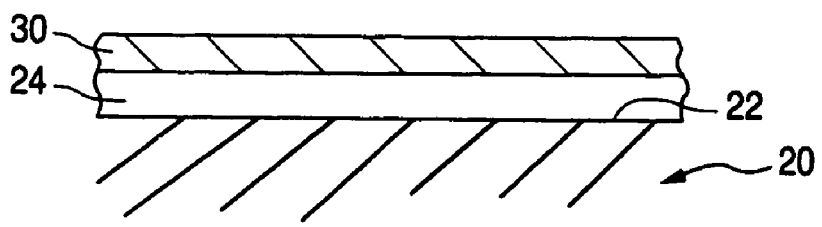

Referring to FIG. 1C, medical substrate 20 is illustrated having active-agent-containing or reservoir layer 24 deposited on surface 22. Barrier layer 30 is formed over at least a selected portion of reservoir layer 24.

Figure 1D:
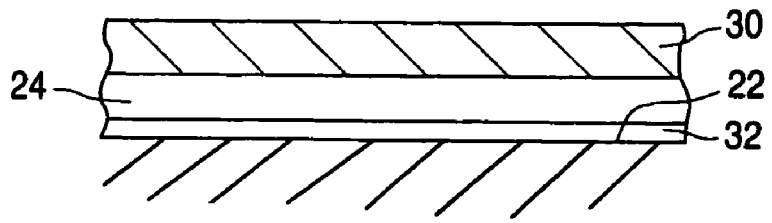

Referring to FIG. 1D, reservoir coating 24 is deposited on a primer layer 32. Barrier layer 30 is formed over at least a portion of reservoir layer 24. Primer layer 32 serves as an intermediary layer for increasing the adhesion between reservoir layer 24 and surface 22. Increasing the amount of active agent admixed within the polymer can diminish the adhesiveness of reservoir layer 24 to surface 22. Accordingly, using an active agent-free polymer as an intermediary primer layer 32 allows for a higher active agent content for reservoir layer 24.

Figure 1E:
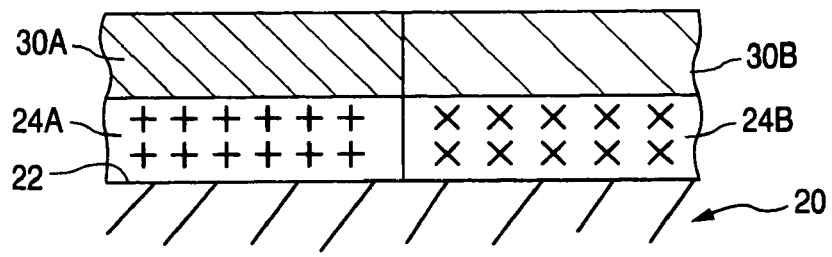

FIG. 1E illustrates medical substrate 20 having a first reservoir layer 24A disposed on a selected portion of surface 22 of medical substrate 20. First reservoir layer 24A contains a first active agent, e.g., 40-O-(2-hydroxy)ethyl-rapamycin. A second reservoir layer 24B can also be disposed on surface 22. Second reservoir layer 24B contains a second active agent, e.g., taxol. First and second reservoir layers 24A and 24B are covered by first and second barrier layers 30A and 30B, respectively. One of ordinary skill in the art can appreciate that barrier layer 30 can be deposited only on selected areas of reservoir layer 24 so as to provide a variety of selected release parameters. Such selected patterns may become particularly useful if a combination of active agents are used, each of which requires a different release parameter.

By way of example, and not limitation, the impregnated reservoir layer 24 can have a thickness of about 0.1 microns to about 20 microns, more narrowly about 0.5 microns to 10 microns. The particular thickness of reservoir layer 24 is based on the type of procedure for which medical substrate 20 is employed and the amount of the active agent to be delivered. The amount of the active agent to be included on medical substrate 20 can be further increased by applying a plurality of reservoir layers 24 on top of one another. Barrier layer 30 can have any suitable thickness, as the thickness of barrier layer 30 is dependent on parameters such as, but not limited to, the desired rate of release and the procedure for which the stent will be used. For example, barrier layer 30 can have a thickness of about 0.1 to about 10 microns, more narrowly from about 0.25 to about 5 microns. Primer layer 32 can have any suitable thickness, examples of which can be in the range of about 0.1 to about 10 microns, more narrowly about 0.1 to about 2 microns.

Fluid Treatment of the Coating

The implantable medical device manufactured in accordance with embodiments of the present invention may be any suitable medical substrate that can be implanted in a human or veterinary patient. In the interests of brevity, methods of manufacturing a drug eluting stent are described herein. However, one of ordinary skill in the art will understand that other medical substrates can be manufactured using the methods of the present invention.

As noted above, the method of the present invention includes applying a fluid to a dry polymeric coating. A stent having a dry polymeric coating can be provided for the fluid treatment process. Alternatively, the dry polymeric coating can be formed on the stent surface as described in further detail herein. The coatings illustrated in FIGS. 1A-1E, for example, can be exposed to the fluid treatment process.

"Dry coating" is defined as a coating with less than about 10% residual fluid (e.g., solvent(s) or water) content (w/w). In one embodiment, the coating has less than about 2% residual fluid content (w/w), and more narrowly, less than about 1% residual fluid content (w/w). The amount of residual fluids in the coating can be determined by a Karl Fisher, or ThermoGravimetric Analysis (TGA), study. For example, a coated stent can be placed in the TGA instrument, and the weight change can be measured at 100° C. as an indication of water content, or measured at a temperature equal to the boiling temperature of the solvent used in the coating as an indication of the solvent content.

"Fluid" is defined as a liquid, vapor or a combination of liquids and/or vapors (i.e., mixture of two or more fluids) that is completely or substantially free from a polymeric substance. In one embodiment, the fluid comprises one or more active agents or drugs. In another embodiment, the fluid is also completely or substantially free from any active agents or drugs. "Substantially free" means that there is more fluid than the other substance (i.e., polymer and/or drug and/or other ingredient) (w/w). In one embodiment, the fluid has less than 0.05% of the substance (i.e., polymer and/or drug and/or other ingredient) (w/w), more narrowly less than 0.01% (w/w) of the substance. "Completely" means that the fluid has 0% (w/w) of such substances.

In one embodiment, the dry coating is subjected to the fluid treatment by applying the fluid to the coating to modify the release rate of the active agent from the coating. In one embodiment, the liquid phase of the fluid should act as or be a solvent for the active agent in the coating by at least partially dissolving the active agent. "Solvent" is defined as a substance capable of dissolving or dispersing one or more other substances or capable of at least partially dissolving or dispersing the substance(s) to form a uniformly dispersed mixture at the molecular- or ionic-size level. When acting as a solvent for the active agent, in one embodiment, the liquid phase of the fluid can be capable of dissolving at least about 5 mg of the active agent in about 1 L of the liquid phase of the fluid at ambient pressure and temperature, and more narrowly, at least about 50 mg of the active agent in about 1 L of the liquid phase of the fluid at ambient pressure and temperature.

Particular polymer and fluid combinations can be selected to desirably affect the polymer morphology and/or drug distribution within the coating in order to modify the release rate of the active agent. For instance, a particular polymer and fluid combination can be selected to cause the polymer in the dry coating to swell as described in Examples 2-4 below. It is also possible to select a combination that advantageously causes the polymer to partially dissolve on the coating. A volatile fluid that partially dissolves the polymer can be used to form a thin membrane of the polymer on the surface of the coating that is substantially free of the active agent.

If the fluid causes the polymer to partially dissolve, the fluid used for the process and the process parameters can be selected to prevent the removal of the polymer from the coating. For example, a fluid can be selected that is a more effective solvent for the active agent than the polymer to prevent the polymer from being removed from the coating. Therefore, some of the active agent can be dissolved in the fluid before the polymer is washed away from the coating. In addition, a volatile fluid, e.g., a fluid having a liquid phase with a boiling temperature below 60° C. at atmospheric pressure, can be selected to prevent the polymer from being removed from the coating.

The fluid treatment can be beneficial because, without the fluid treatment, the active agent (e.g., 40-O-(2-hydroxy)ethyl-rapamycin) can diffuse from the polymer matrix at a rate that could be too high for certain clinical conditions. For example, by using the process of the present invention, a fluid can be applied to the dry coating for a sufficient duration effective to decrease the release rate of 40-O-(2-hydroxy)ethyl-rapamycin, or analog or derivative thereof, by about 50% as compared to a control group, as demonstrated in Example 3 below.

Without being bound by any particular theory, it is believed that the diffusion rate of the active agent from the polymer of the present invention can be modified because the fluid treatment modifies the polymer morphology and/or redistributes the solid state concentration of the active agent within the dry coating. For example, in one embodiment of the present invention, the fluid used for the treatment causes the polymer in the coating to swell, and at the same time, solubilizes the active agent in the coating. The fluid therefore extracts a portion of the active agent from the surface layer of the coating, and causes the polymer to redistribute at the surface of the coating to form a thin membrane on the surface that is substantially free of the active agent. The thin membrane of the polymer at the surface can reduce the release rate of the active agent from the deeper regions in the final coating.

In another embodiment of the present invention, the dry coating is subjected to a fluid treatment by applying a pure fluid to the coating for a sufficient duration to increase the percent crystallinity of the polymer in the coating. Methods of determining the percent crystallinity of the polymer are described below.

By increasing the percent crystallinity of the polymer in the coating, the fluid treatment process can address some of the shortcomings of conventional coating techniques. For instance, the diffusion rate of the active agent from the polymer of the present invention, for example, can be modified by selecting a fluid which increases the percent crystallinity of the polymer in the coating without substantially extracting the drug.

By increasing the percent crystallinity of the polymer in the coating, the fluid treatment process of the present invention can also increase the manufacturing consistency of drug eluting stents by reducing the variability of the release rate of active agents among stents. By exposing a stent coating to a fluid treatment process, for example, it is believed that the standard deviation of the mean release rate of the active agent in a 24 hour period can be decreased so that the standard deviation is lower than the standard deviation of the mean release rate for a baseline group of stents (i.e., stents which have not been subjected to a fluid treatment process).

Without being bound by any particular theory, it is believed that the fluid treatment process can increase manufacturing consistency by moving a polymeric stent coating closer to a kinetic or thermodynamic equilibrium. For example, typically if a semicrystalline polymer is employed in the coating composition, when volatile solvents are used in the coating composition, the polymer does not have an opportunity to fully crystallize before the solvent is removed to form the dry coating. The fluid treatment process can be used to improve polymer morphology by increasing the percent crystallinity of the polymer.

The fluid treatment process can also reduce the release rate drift over time by increasing the percent crystallinity of the polymer in the coating. "Release rate drift" refers to the phenomenon in which the release rate of an active agent from a polymeric coating can change over time, for instance while the stent is in storage. Release rate drift may occur because of changes in the morphology of a polymeric coating over a period of time, for example if the polymeric coating is exposed to degradation agents such as oxygen and moisture. The fluid treatment process can increase the percent crystallinity of the polymer so that the polymer is in a thermodynamically or kinetically stable state, thereby reducing the changes in the morphology of a polymeric coating over time. The solvent treatment process, therefore, can improve the self life of the stent product.

"Percent crystallinity" refers to the percentage of the polymer material that is in a crystalline form. In one embodiment of the present invention, the polymer is a semicrystalline polymer having between 10 and 75 percent crystallinity. For example, poly(vinylidene fluoride-co-hexafluoroisopropylene) can achieve about 20% crystallinity when the vinylidene fluoride to hexafluoroisopropylene ratio is 85:15. Also, by example, poly(vinylidene fluoride) can achieve about a 65 percent crystallinity, and poly(6-aminocaproic acid) can achieve about a 64 percent crystallinity.

Those of ordinary skill in the art understand that there are several methods for determining the percent crystallinity in polymers. These methods are, for example, described in L. H. Sperline, Introduction to Physical Polymer Science (3rd ed. 2001). The first involves the determination of the heat of fusion of the whole sample by calorimetric methods. The heat of fusion per mole of crystalline material can then be estimated independently by melting point depression experiments. The percent crystallinity is then given by heat of fusion of the whole sample divided by the heat of fusion per mole of crystalline material times 100.

A second method involves the determination of the density of the crystalline portion via X-ray analysis of the crystal structure, and determining the theoretical density of a 100% crystalline material. The density of the amorphous material can be determined from an extrapolation of the density from the melt to the temperature of interest. Then the percent crystallinity is given by:

$$\% \text{ Crystallinity} = \frac{\rho_{exptl} - \rho_{amorph}}{\rho_{100\% \ cryst} - \rho_{amorph}} \times 100$$

where $\rho_{exptl}$ represents the experimental density, and $\rho_{amorph}$ and $\rho_{100\% \ cryst}$ are the densities of the amorphous and crystalline portions, respectively.

A third method stems from the fact that X-ray diffraction depends on the number of electrons involved and is thus proportional to the density. Besides Bragg diffraction lines for the crystalline portion, there is an amorphous halo caused by the amorphous portion of the polymer. The amorphous halo occurs at a slightly smaller angle than the corresponding crystalline peak, because the atomic spacings are larger. The amorphous halo is broader than the corresponding crystalline peak, because of the molecular disorder. This third method can be quantified by the crystallinity index, CI, where $$CI = \frac{A_c}{A_a + A_c}$$

and where $A_c$ and $A_a$ represent the area under the Bragg diffraction line and corresponding amorphous halo, respectively.

Representative examples of fluids for the treatment process include chloroform, acetone, water (buffered saline), dimethylsulfoxide, propylene glycol methyl ether, iso-propylalcohol, n-propylalcohol, methanol, ethanol, tetrahydrofuran, dimethylformamide, dimethylacetamide, benzene, toluene, xylene, hexane, cyclohexane, pentane, heptane, octane, nonane, decane, decalin, ethyl acetate, butyl acetate, isobutyl acetate, isopropyl acetate, butanol, diacetone alcohol, benzyl alcohol, 2-butanone, cyclohexanone, dioxane, methylene chloride, carbon tetrachloride, tetrachloroethylene, tetrachloro ethane, chlorobenzene, 1,1,1-trichloroethane, formamide, hexafluoroisopropanol, 1,1,1-trifluoroethanol, acetonitrile, and hexamethyl phosphoramide and a combination thereof.

The fluid can be applied by immersing the stent in the fluid. The stent can be immersed in the fluid, for example, for about ten seconds to about thirteen hours, more narrowly about 30 minutes to about twelve hours. The stent should be immersed for a sufficient duration to effect the desired changes in the polymer morphology and/or drug distribution.

The fluid can also be applied by spraying the fluid onto the stent with a conventional spray apparatus, or applied by other metering devices. For instance, the stent can be sprayed for one to ten spray cycles (i.e., back and forth passes along the length of the stent) using a spray apparatus to deposit about 1 ml to about 500 ml, more narrowly 5 ml to about 20 ml, of the fluid onto the stent. The spray process can take place in a vacuum chamber at a reduced pressure (e.g., less than 300 mm Hg) in order to raise the fluid concentration in the vapor phase. As above, the stent should be exposed to the fluid spray process for a sufficient duration to effect the desired changes in the polymer morphology.

The fluid treatment should not adversely affect the characteristics of the active agent present in the coating. In order to prevent possible degradation of the active agents or the polymers in the coating, the fluid should not react with the active agent in the coating. Additionally, the fluid should not cause the active agent to crystallize within the dry polymeric coating. Crystallization of the active agent may disadvantageously change the release rate of the active agent from the coating when implanted into a biological lumen.

Subsequent to the fluid treatment process, the coating should be allowed to dry to substantially remove the fluid. For instance, the removal of the fluid can be induced by baking the stent in an oven at a mild temperature (e.g., 60° C.) for a suitable duration of time (e.g., 2-4 hours).

In one embodiment of the present invention, the fluid treatment is directed to selected portions of the drug eluting stent. By directing the fluid treatment to only portions of the stent coating, the stent coating can have a variable drug release profile, for example along the length of the stent. For instance, the release rate at the end segments of the stent can be reduced relative to the release rate from middle segment of the stent by applying the fluid only to the end segments of the stent.

The fluid treatment process parameters are selected to limit the penetration of the fluid into the thickness of the coating. By limiting the treatment process, a coating can be produced in which the shallower regions of the coating have a different coating morphology than the deeper regions. For example, a volatile fluid (e.g., acetone) or a limited process duration can be used so that most of the fluid is evaporated before penetrating into the deep regions of the coating. One of ordinary skill in the art will understand that the fluids chosen or the duration of the fluid treatment will depend on factors such as the desired diffusion rate of the active agent through the polymer, and the inherent characteristics of the polymers and active agents used in the coating.

In another embodiment of the present invention, the fluid used for the treatment is heated to a temperature greater than room temperature as the fluid is applied to the polymeric coating. The temperature used should be below the temperature that significantly degrades the active agent disposed in the coating.

In one embodiment, the polymer in the coating is a semicrystalline polymer (e.g., polyvinyl chloride or an ethylene vinyl alcohol copolymer), and the fluid is heated to the crystallization temperature ($T_c$) of the polymer as the fluid is applied to the polymeric coating. "Crystallization temperature" refers to the temperature at which a semicrystalline polymer has its highest percent crystallinity. Amorphous polymers do not exhibit a crystallization temperature. Methods of determining a crystallization temperature are described below. The crystallization temperature of ethylene vinyl alcohol copolymer (44 mole % ethylene), for instance, is about 415° K (ethylene vinyl alcohol copolymer ("EVAL") is commonly known by the generic name EVOH or by the trade name EVAL). Other examples of crystallization temperatures include 396° K for poly(ethylene terephthalate) as measured by differential scanning calorimetry (as reported by Parravicini et al., J. Appl. Polym. Sci., 52(7), 875-85 (1994); and 400° K for poly(p-phenylene sulfide) as measured by differential scanning calorimetry (as reported by Ding et al. Macromolecules, 29(13), 4811-12 (1996)).

In another embodiment of the present invention, the fluid applied to the dry polymeric coating is heated so that the dry coating is exposed to a temperature equal to or greater than the $T_g$ of the polymer in the coating. Both amorphous and semicrystalline polymers exhibit glass transition temperatures. Additionally, if the polymer is a semicrystalline polymer, the dry polymeric coating can be exposed to a temperature equal to or greater than the $T_g$ but less than the melting temperature ($T_m$) of the polymer in the coating. Amorphous polymers do not exhibit a $T_m$.

The $T_g$ is the temperature at which the amorphous domains of a polymer change from a brittle vitreous state to a plastic state at atmospheric pressure. In other words, the $T_g$ corresponds to the temperature where the onset of segmental motion in the chains of the polymer occurs. When an amorphous or semicrystalline polymer is exposed to an increasing temperature, the coefficient of expansion and the heat capacity of the polymer both increase as the temperature is raised, indicating increased molecular motion. As the temperature is raised the actual molecular volume in the sample remains constant, and so a higher coefficient of expansion points to an increase in free volume associated with the system and therefore increased freedom for the molecules to move. The increasing heat capacity corresponds to an increase in heat dissipation through movement.

Figure 3:
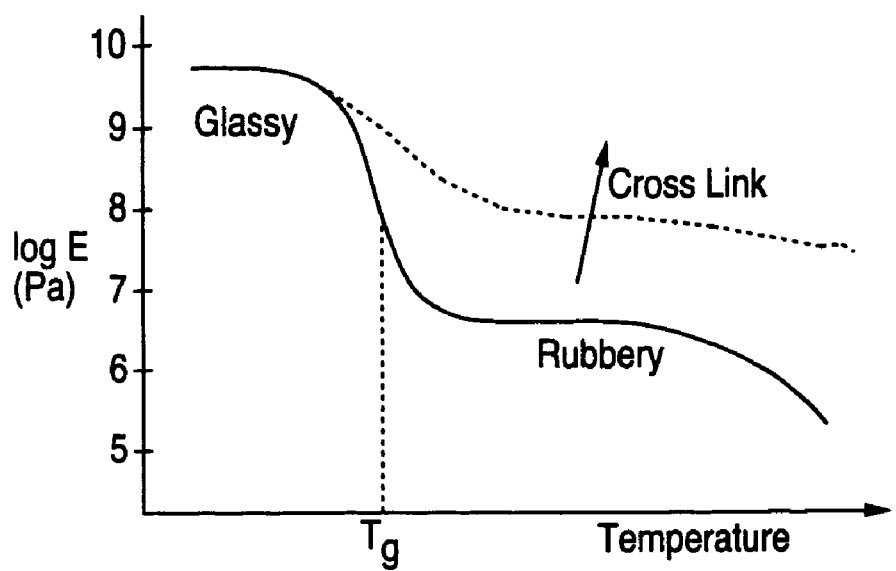
FIG. 3 is graph of the relationship of elasticity versus temperature for a polymer.

$T_g$ of a given polymer can be dependent on the heating rate and can be influenced by the thermal history of the polymer. Furthermore, the chemical structure of the polymer heavily influences the glass transition by affecting mobility. Generally, flexible main-chain components lower the $T_g$; bulky side-groups raise the $T_g$; increasing the length of flexible side-groups lowers the $T_g$; and increasing main-chain polarity increases the $T_g$. Additionally, the presence of crosslinking polymeric components can increase the observed $T_g$ for a given polymer. For instance, FIG. 3 illustrates the effect of temperature and crosslinking on the modulus of elasticity of a polymer, showing that forming cross-links in a polymer can increase the $T_g$ and shift the elastic response to a higher plateau-one that indicates that the polymer has become more glassy and brittle. Moreover, molecular weight can significantly influence $T_g$, especially at lower molecular weights where the excess of free volume associated with chain ends is significant.

The $T_m$ of a polymer, on the other hand, is the temperature at which the last trace of crystallinity in a polymer disappears as a sample is exposed to increasing heat. The $T_m$ of a polymer is also know as the fusion temperature ($T_f$). The $T_m$ is always greater than the $T_g$ for a given polymer.

Like the $T_g$, the melting temperature of a given polymer is influenced by the structure of the polymer. The most influential inter- and intramolecular structural characteristics include structural regularity, bond flexibility, close-packing ability, interchain attraction. In general, high melting points are associated with highly regular structures, rigid molecules, close-packing capability, strong interchain attraction, or two or more of these factors combined.

Figure 2:
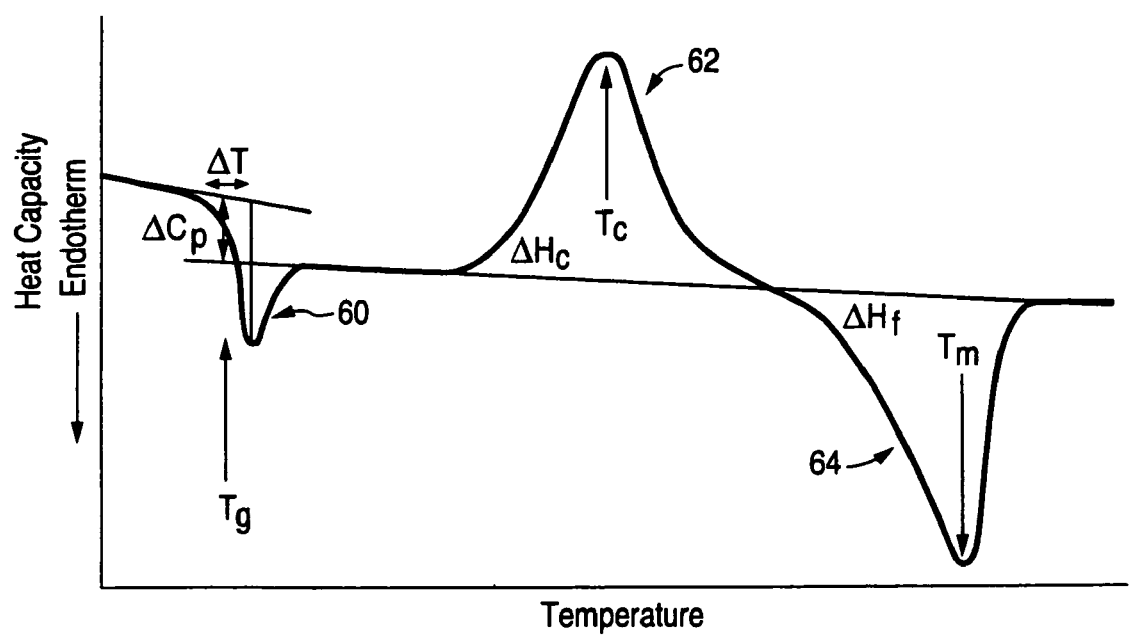
FIG. 2 is a graph of the relationship of heat capacity versus temperature for a polymer.

Referring to FIG. 2, if the coating polymer is a semicrystalline polymer, as the polymeric coating is exposed to an increasing temperature, the polymer exhibits three characteristic thermal transitions represented by first curve 60, second curve 62 and third curve 64. FIG. 2 illustrates the change in heat capacity (endothermic v. exothermic) of a semicrystalline polymer as the polymer is exposed to an increasing temperature, as measured by the differential scanning calorimetry (DSC) method. DSC uses the relationship between heat capacity and temperature as the basis for determining the thermal properties of polymers and is further described below.

By way of illustration, when a semicrystalline polymer is exposed to an increasing temperature, the crystallinity of the polymer begins to increase as the increasing temperature reaches the $T_g$. At and above the $T_g$, the increased molecular motion of the polymer allows the polymer chains to move around more to adopt a more thermodynamically stable relationship, and thereby increase the percent crystallinity of the polymer sample. In FIG. 2, the $T_g$ is shown as point $T_g$ of first curve 60, which is the temperature at which half of the increase in heat capacity ($\Delta C_p$) has occurred. The percent crystallinity then increases rapidly after point $T_g$ and is maximized at the $T_c$ of the polymer, which is indicated at the point $T_c$ (the apex of second curve 62). As the temperature continues to increase, the temperature approaches the melting temperature ($T_m$) of the polymer, and the percent crystallinity decreases until the temperature reaches the melting temperature of the polymer (at point $T_m$ of curve 64). As noted above, $T_m$ is the temperature where the last trace of crystallinity in the polymer disappears. The heat of crystallization, $\Delta H_c$, and the heat of fusion, $\Delta H_f$, can be calculated as the areas under curves 62 and 64. The heat of crystallization and heat of fusion must be equal, but with opposite signs.

The $T_g$ and/or the $T_m$ of the polymer that is to be exposed to the fluid treatment should be determined experimentally in order to determine which temperatures can be used to treat the dry polymeric coating with the heated fluid. As used herein, "test polymer" means the polymer that is measured to determine the $T_g$ and/or the $T_m$ of the polymer. "Coating polymer" means the polymer that is actually applied as a component of the stent coating.

In order to accurately characterize the thermal properties of the coating polymer, one should consider the number of factors that can influence the $T_g$ and $T_m$ of a polymer. In particular, the factors include (1) the structure of the polymer (e.g., modification of side groups and dissimilar stereoregularity); (2) the molecular weight of the polymer; (3) the molecular-weight distribution ($M_w/M_n$) of the polymer; (4) the crystallinity of the polymer; (5) the thermal history of the polymer; (6) additives or fillers that are included in the polymer; (7) the pressure applied to the polymer as the polymer is heated; (8) residual fluids in the polymer and (9) the rate that the polymer is heated.

One can account for the foregoing factors by using a test polymer that is substantially the same as the coating polymer, and is tested under substantially the same conditions as the conditions used to conduct the fluid treatment of the polymeric coating. The test polymer should have the same chemical structure as the coating polymer, and should have substantially the same molecular weight and molecular-weight distribution as the coating polymer. For example, if the polymer is a blend of copolymers or homopolymers, the test polymer should have substantially the same percentage of components as the coating polymer. At the same time, the test polymer should have substantially the same crystallinity as the coating polymer. Methods of determining crystallinity are discussed herein. Additionally, the composition used to form the test polymer should include the same compounds (e.g., additives such as therapeutic substances) and liquids (e.g., solvent(s) and water) that are mixed with the coating polymer. Moreover, the test polymer should have the same thermal history as the coating polymer. The test polymer should be prepared under the same conditions as the coating polymer, such as using the same solvent, temperature, humidity and mixing conditions. Finally, the heating rate used for measuring the transition temperature of the test polymer should be substantially similar to the heating rate used to conduct the fluid treatment of the polymeric coating.

The $T_g$ and $T_m$ of the test polymer can be measured experimentally by testing a bulk sample of the polymer. As understood by one of ordinary skill in the art, a bulk sample of the polymer can be prepared by standard techniques, for example those that are outlined in the documentation accompanying the instruments used to measure the transition temperature of the polymer.

There are several methods that can be used to measure the $T_g$ and $T_m$ of a polymer. The $T_g$ and $T_m$ can be observed experimentally by measuring any one of several basic thermodynamic, physical, mechanical, or electrical properties as a function of temperature. Methods of measuring glass transition temperatures and melting temperatures are understood by one of ordinary skill in the art and are discussed by, for example, L. H. Sperling, Introduction to Physical Polymer Science, Wiley-Interscience, New York (3rd ed. 2001), and R. F. Boyer, in Encyclopedia of Polymer Science and Technology, Suppl. Vol. 2, N. M. Bikales, ed., Interscience, New York (1977).

Figure 4:
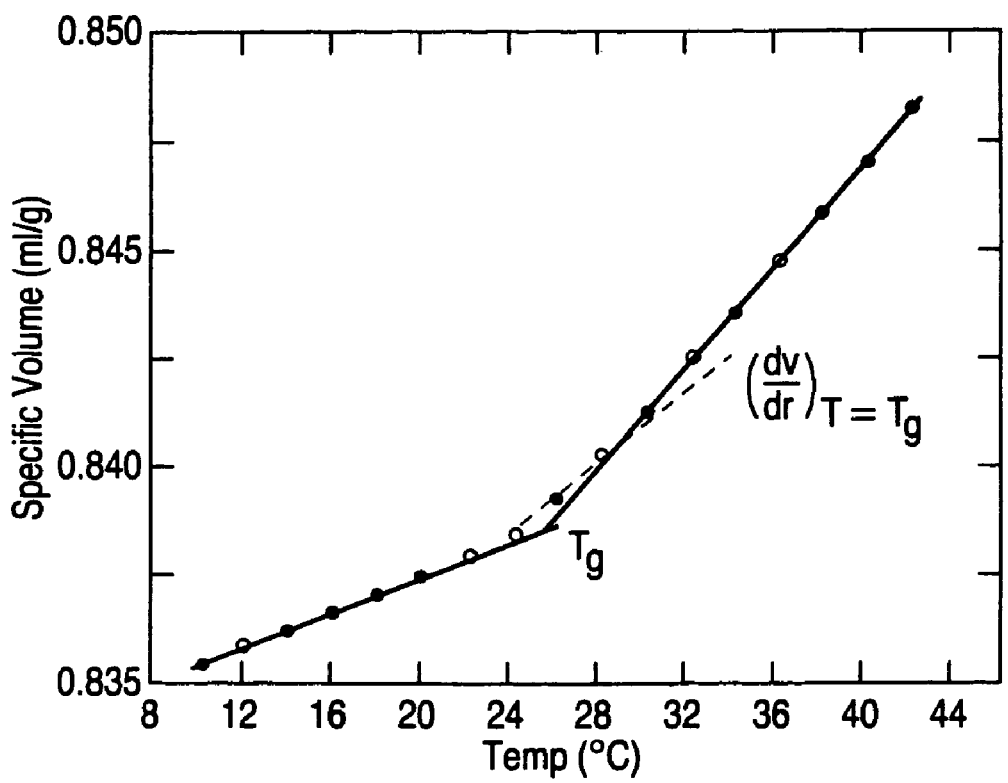
FIG. 4 is a graph of the relationship of specific volume versus temperature for a polymer.

The $T_g$ of a bulk sample can be observed by measuring the expansion of the polymer as the polymer is exposed to increasing temperature. This process is known as dilatometry. There are two ways of characterizing polymers via dilatometry. One way is to measure the linear expansivity of the polymer sample. Another method involves performing volume-temperature measurements, where the polymer is confined by a liquid and the change in volume is recorded as the temperature is raised. The usual confining liquid is mercury, since it does not swell organic polymers and has no transition of its own through most of the temperature range of interest. The results may be plotted as specific volume versus temperature as shown in FIG. 4, which illustrates a representative example of a dilatometric study of branched poly(vinyl acetate). Since the elbow in volume-temperature studies is not sharp (measurements of $T_g$ using dilatometric studies show a dispersion of about 20-30° C.), the two straight lines below and above the transition are extrapolated until they meet. The extrapolated meeting point is taken as the $T_g$. A representative example of an apparatus that can be used to measure a $T_g$ via dilatometric studies is the Dilatometer DIL 402 PC (available from Netzschu, Inc., Exton, Pa.).

Thermal methods can also be used to measure the $T_g$ of a bulk sample. Two closely related methods are differential thermal analysis (DTA), and differential scanning calorimetry (DSC). Both methods yield peaks relating to endothermic and exothermic transitions and show changes in heat capacity. A representative example of a DTA apparatus is the Rheometrics STA 1500 which provides simultaneous thermal analysis via DTA and DSC.

In addition to the information that can be produced by a DTA, the DSC method also yields quantitative information relating to the enthalpic changes in the polymer (the heat of fusion of the temperature, $\Delta H_f$). The DSC method uses a servo system to supply energy at a varying rate to the sample and the reference, so that the temperatures of the two stay equal. The DSC output plots energy supplied against average temperature. By this method, the areas under the peaks can be directly related to the enthalpic changes quantitatively.

Referring to FIG. 2, the $T_g$ can be taken as the temperature at which one-half of the increase in the heat capacity, $\Delta C_p$, has occurred. The increase in $\Delta C_p$ is associated with the increased molecular motion of the polymer.

A method of separating a transient phenomenon such as a hysteresis peak from the reproducible result of the change in heat capacity is obtained via the use of modulated DSC. Here, a sine wave is imposed on the temperature ramp. A real-time computer analysis allows a plot of not only the whole data but also its transient and reproducible components. Representative examples of modulated DSC apparatuses are those in the Q Series™ DSC product line from TA Instruments, New Castle, Del.

Another representative example of an apparatus that uses DSC as the base technology for measuring the $T_g$ is a micro thermal analyzer, such as the μTA™ 2990 product from TA Instruments. A micro thermal analyzer can have an atomic force microscope (AFM) that is used in conjunction with a thermal analyzer. The instrument can be used to analyze individual sample domains identified from the AFM images. In a micro thermal analyzer such as the μTA™ 2990, the AFM measurement head can contain an ultra-miniature probe that functions as a programmable heat source and temperature sensor. A micro thermal analyzer, therefore, can provide information similar to that from traditional thermal analysis, but on a microscopic scale. For example, the μTA™ 2990 can provide images of a sample in terms of its topography, relative thermal conductivity and relative thermal diffusivity. The μTA™ 2990 can also provide spatial resolution of about 1 μm with a thermal probe and atomic resolution with regular AFM probes. Other advantages of the μTA™ 2990 is that it can heat the polymer sample from ambient to about 500° C. at heating rates up to 1500° C./minute which allows for rapid thermal characterization (e.g., in less than 60 seconds), and it can hold the sample isothermically over a broad range of temperatures (e.g., −70 to 300° C.), which allows for thermal characterization over a broad temperature range.

Since the notion of the glass-rubber transition stems from a softening behavior, mechanical methods can provide very direct determination of the $T_g$ for a bulk sample. Two fundamental types of measurement prevail: the static or quasi-static methods, and the dynamic methods. For amorphous polymers and many types of semicrystalline polymers in which the crystallinity does not approach 100%, stress relaxation, Gehman, and/or Glash-Berg instrumentation provide, through static measurement methods, rapid and inexpensive scans of the temperature behavior of new polymers before going on to more complex methods. Additionally, there are instruments that can be employed to measure dynamic mechanical spectroscopy (DMS) or dynamic mechanical analysis (DMA) behavior. A representative example of an apparatus for a DMA method is the DMA 242, available from Netzsch, Inc., Exton, Pa.

Another method for studying the mechanical spectra of all types of polymers, especially those that are not self-supporting, is torsional braid analysis (TBA). In this case the polymer is dipped onto a glass braid, which supports the sample. The braid is set into a torsional motion. The sinusoidal decay of the twisting action is recorded as a function of time as the temperature is changed. Because the braid acts as a support medium, the absolute magnitudes of the transitions are not obtained; only their temperatures and relative intensities are recorded.

The $T_g$ of a bulk sample of a polymer can also be observed by utilizing electromagnetic methods. Representative examples of electromagnetic methods for the characterization of transitions in polymers are dielectric loss (e.g., using the DEA 2970 dielectric analyzer, available from TA Instruments, New Castle, Del.) and broad-line nuclear magnetic resonance (NMR).

If the thickness of the coating polymer is ultra thin (i.e., less than 1 micron), it may be useful to utilize specialized measuring techniques, at least to compare the results with the values determined by measuring a bulk polymer sample to ensure that the bulk values are not affected by the thickness of the polymer layer. Specialized techniques may be useful because it has recently been observed that the $T_g$ of a polymer can be influenced by the thickness of the polymer layer. Researchers, for example, have observed that polystyrene films on hydrogen-passivated Si had glass transition temperatures that were lower than the bulk value if the thickness of the films was less than 0.04 microns. See Forest et al., Effect of Free Surfaces on the $T_g$ of Thin Polymer Films, Physical Review Letters 77(10), 2002-05 (September 1996).

Brillouin light scattering (BLS) can be used to measure the $T_g$ of a polymer in an ultra thin film. The ultra thin films can be prepared by spin casting the polymer onto a substrate (e.g., the same substrate used to support the coating polymer on the stent). A spinning apparatus is available, for example, from Headway Research, Inc., Garland, Tex. BLS can also be used to find the $T_g$ of a polymer in a bulk sample. In BLS studies of bulk polymers, one measures the velocity $v_L$ of the bulk longitudinal phonon, where $v_L=(C_{11}/\rho)^{1/2}$, $C_{11}$ is the longitudinal elastic constant, and $\rho$ is the density. Since $C_{11}$ is a strong function of $\rho$, as the sample temperature is changed, the temperature dependence of $v_L$ exhibits an abrupt change in slope at the temperature at which the thermal expansivity is discontinuous, i.e., the $T_g$. For thin films, BLS probes the elastic properties through observation of film-guided acoustic phonons. The guided acoustic modes are referred to as Lamb modes for freely standing films. For further discussion of the application of BLS for measuring $T_g$, see Forest et al., Effect of Free Surfaces on the Glass Transition Temperature of Thin Polymer Films, Physical Review Letters 77(10), 2002-05 (September 1996) and Forest et al. Mater. Res. Soc. Symp. Proc. 407, 131 (1996).

The $T_g$ of an ultra thin polymer film can also be determined by using three complementary techniques: local thermal analysis, ellipsometry and X-ray reflectivity. See, e.g., Fryer et al., Dependence of the Glass Transition Temperature of Polymer Films on Interfacial Energy and Thickness, Macromolecules 34, 5627-34 (2001). Using ellipsometry (e.g., with a Rudolph Auto E1 nulling ellipsometer) and X-ray reflectivity (e.g., with a Scintag XDS 2000), the $T_g$ is determined by measuring changes in the thermal expansion of the film. Using local thermal analysis, on the other hand, the $T_g$ is determined by measuring changes in the heat capacity and thermal conductivity of the film and the area of contact between a probe and the polymer surface.

Table 1 lists the $T_g$ for some of the polymers used in the embodiments of the present invention. The cited temperature is the temperature as reported in the noted reference and is provided by way of illustration only and is not meant to be limiting.

TABLE 1

| POLYMER | $T_g$ (° K) | METHOD USED TO CALCULATE $T_g$ | REFERENCE |
|---|---|---|---|
| EVAL | 330 | DMA | Tokoh et al., Chem. Express, 2(9), 575-78 (1987) |
| Poly(n-butyl methacrylate) | 293 | Dilatometry | Rogers et al., J. Phys. Chem., 61, 985-90 (1957) |
| Poly(ethylene-co-vinyl acetate) | 263 | DSC and DMA | Scott et al., J. Polym. Sci., Part A, Polym. Chem., 32(3), 539-55 (1994) |
| Poly(ethylene terephthalate) | 343.69 | DSC | Sun et al., J. Polym. Sci., Part A, Polym. Chem., 34(9), 1783-92 (1996) |
| Poly(vinylidene fluoride) | 243 | Dielectric relaxation | Barid et al., J. Mater. Sci., 10(7), 1248-51 (1975) |
| Poly(p-phenylene sulfide) | 361 | DSC | Ding, et al., Macromolecules, 29(13), 4811-12 (1996) |
| Poly(6-aminocaproic acid) | 325 | DSC | Gee et al., Polymer, 11, 192-97 (1970) |
| Poly(methyl methacrylate) | 367 | DSC | Fernandez-Martin, et al., J. Polym. Sci., Polym. Phys. Ed., 19(9), 1353-63 (1981) |
| Poly(vinyl alcohol) | 363 | Dilatometry | Fujii et al., J. Polym. Sci., Part A, 2, 2327-47 (1964) |
| Poly(epsilon-caprolactone) | 208 | DSC | Loefgren et al., Macromolecules, 27(20), 5556-62 (1994) |

As noted above, "polymer" as used herein is inclusive of homopolymers, copolymers, terpolymers etc., including random, alternating, block, cross-linked, blends and graft variations thereof. By using the methods of measurement described above, one may observe more than one $T_g$ for some of these types of polymers. For example, some polymer blends that exhibit two phase systems can have more than one $T_g$. Additionally, some semicrystalline polymers can have two glass transitions, especially when they have a higher percent crystallinity. See Edith A. Turi, Thermal Characterization of Polymeric Materials, Academic Press, Orlando, Fla. (1981). Bulk-crystallized polyethylene and polypropylene, for example, can have two glass transition temperatures at a relatively high percent crystallinity. The lower of the two transitions is represented as $T_g(L)$, which can be the same as the conventional $T_g$ at zero crystallinity. The higher transition is designated as $T_g(U)$ and becomes more detectable as the crystallinity increases. The difference, $\Delta T_g=T_g(U)-T_g(L)$, tends to approach zero as the fractional crystallinity X approaches zero.

It has also been reported that block and graft copolymers can have two separate glass transition temperatures. For some of these polymers, each $T_g$ can be close to the $T_g$ of the parent homopolymer. The following Table 2 lists the glass transition temperatures for representative examples of block and graft copolymers. As illustrated by Table 2, most of these block and graft copolymers exhibit two glass transition temperatures. The cited temperatures were reported in Black and Worsfold, J. Appl. Polym. Sci., 18, 2307 (1974) who used a thermal expansion technique to measure the temperatures, and are provided by way of illustration only.

TABLE 2

| $M_1$ | $M_2$ | % $M_1$ | Total MW | Lower $T_g$ (° K) | Upper $T_g$ (° K) |
|---|---|---|---|---|---|
| α-Methylstyrene | Vinyl acetate | 18 | 103,000 | 308 | 455 |
| α-Methylstyrene | Vinyl chloride | 67 | 39,000 | 265 | 455 |
| α-Methylstyrene | Styrene | 45 | 61,000 | 400 | — |
| Styrene | Methyl methacrylate | 40 | 70,000 | — | 371 |
| Styrene | Butyl acrylate | 46 | 104,000 | 218 | 372 |
| Styrene | Ethylene oxide | 50 | 40,000 | 201 | 373 |
| Styrene | Isoprene | 50 | 1,000,000 | 198 | 374 |
| Styrene | Isobutylene | 40 | 141,000 | 204 | 375 |
| Methyl Methacrylate | Ethyl acrylate | 56 | 162,000 | 250 | 388 |
| Methyl Methacrylate | Vinyl acetate | 50 | 96,000 | 311 | 371 |
| Methyl Methacrylate | Ethyl methacrylate | 50 | 104,000 | 342 | 379 |

In one embodiment of the present invention, if the polymer exhibits more than one $T_g$, the fluid is heated to exposed the polymer to a temperature equal to or greater than the lowest observed $T_g$. It is believed that by exposing a polymer to a temperature equal to or greater than the lowest $T_g$, the release rate of the polymer should be reduced to a measurable extent because at least some of the amorphous domains will be modified during the process. In another embodiment, if the polymer exhibits more than one $T_g$, the fluid is heated to expose the polymer to a temperature equal to or greater than the highest observed $T_g$. By exposing the polymer to the highest $T_g$, it is believed that one can maximize the release rate reduction.

As noted above, in one embodiment, the drug polymeric drug coating can be exposed to a temperature equal to or greater than the $T_g$ lower than the $T_m$ of the polymer. There are several types of methods that can be used to measure the $T_m$ of a polymer. For example, the melting temperature can be observed by measuring visual, physical, and thermal properties as a function of temperature.

$T_m$ can be measured by visual observation by using microscopic techniques. For instance, the disappearance of crystallinity in a semicrystalline or crystalline polymer can be observed with a microscope, with the sample housed between crossed nicols (i.e., an optical material that functions as a prism, separating light rays that pass through it into two portions, one of which is reflected away and the other transmitted). As a polymer sample is heated, the sharp X-ray pattern characteristic of crystalline material gives way to amorphous halos at the $T_m$.

Another way of observing the $T_m$ is to observe the changes in specific volume with temperature. Since melting constitutes a first-order phase change, a discontinuity in the volume is expected. The $T_m$ should give a discontinuity in the volume, with a concomitant sharp melting point. Because of the very small size of the crystallites in bulk crystallized polymers, however, most polymers melt over a range of several degrees. The $T_m$ is the temperature at which the last trace of crystallinity disappears. This is the temperature at which the largest and/or most "perfect" crystals are melting.

Alternatively, the $T_m$ can be determined by using thermomechanical analysis (TMA) that uses a thermal probe (e.g., available from Perkin Elmer, Norwalk, Conn.). The $T_m$ can also be determined with a thermal-based method. For example, a differential scanning calorimetry (DSC) study can be used to determine the $T_m$. The same process for DSC as described above for the determination of $T_g$ can be used to determine the $T_m$. Referring to FIG. 2, the $T_m$ of the representative polymer is the peak of curve 64.

Table 3 lists the melting temperatures for some of the polymers used in the embodiments of the present invention. The cited temperature is the temperature as reported in the noted reference and is provided by way of illustration only and is not meant to be limiting.

TABLE 3

| POLYMER | $T_m$ (° K) | METHOD USED TO CALCULATE $T_m$ | REFERENCE |
|---|---|---|---|
| EVAL | 437.3 | DMA | Tokoh et al., Chem. Express, 2(9), 575-78 (1987) |
| Poly(ethylene terephthalate) | 526.38 | DSC | Sun et al., J. Polym. Sci., Part A, Polym. Chem., 34(9), 1783-92 (1996) |
| Poly(vinylidene fluoride) | 444 | Dielectric relaxation | Barid et al., J. Mater. Sci., 10(7), 1248-51 (1975) |
| Poly(p-phenylene sulfide) | 560 | DSC | Ding, et al., Macromolecules, 29(13), 4811-12 (1996) |
| Poly(6-aminocaproic acid) | 498 | DSC | Gee et al., Polymer, 11, 192-97 (1970) |
| Poly(vinyl alcohol) | 513 | TMA | Fujii et al., J. Polym. Sci., Part A, 2, 2327-47 (1964) |
| Poly(epsilon-caprolactone) | 330.5 | DSC | Loefgren et al., Macromolecules, 27(20), 5556-62 (1994) |

In the embodiments of the present invention, the fluid treatment process can be used to reduced the release rate of an active agent from polymeric coatings having various coating structures. Referring to FIG. 1A, for instance, reservoir layer 24 has a polymer and an active agent. The polymer in reservoir layer 24 can be exposed to a fluid sufficient to reduce the release rate of the active agent from reservoir layer 24.

The fluid treatment process can also be directed to a coating having a barrier layer as illustrated in FIGS. 1B-1E. Referring to FIG. 1B, for instance, an active agent can be deposited in cavities 26, and covered by barrier layer 30. In one embodiment of the present invention, the polymer in barrier layer 30 is subjected to the fluid treatment process.

Forming an Active Agent-Containing Coating

The composition containing the active agent can be prepared by first forming a polymer solution by adding a predetermined amount of a polymer to a predetermined amount of a compatible solvent. The polymer can be added to the solvent at ambient pressure and under anhydrous atmosphere. If necessary, gentle heating and stirring and/or mixing can be employed to effect dissolution of the polymer into the solvent, for example 12 hours in a water bath at about 60° C.

Sufficient amounts of the active agent can then be dispersed in the blended composition of the polymer and the solvent. The active agent should be in true solution or saturated in the blended composition. If the active agent is not completely soluble in the composition, operations including mixing, stirring, and/or agitation can be employed to effect homogeneity of the residues. The active agent can also be first added to a compatible solvent prior to admixing with the composition.

The polymer can comprise from about 0.1% to about 35%, more narrowly from about 0.5% to about 20% by weight of the total weight of the composition, the solvent can comprise from about 59.9% to about 99.8%, more narrowly from about 79% to about 99% by weight of the total weight of the composition, and the active agent can comprise from about 0.1% to about 40%, more narrowly from about 1% to about 9% by weight of the total weight of the composition. Selection of a specific weight ratio of the polymer and solvent is dependent on factors such as, but not limited to, the material from which the device is made, the geometrical structure of the device, and the type and amount of the active agent employed.

Representative examples of polymers that can be combined with the active agent for the reservoir layer include ethylene vinyl alcohol copolymer (commonly known by the generic name EVOH or by the trade name EVAL); polybutylmethacrylate; poly(ethylene-co-vinyl acetate); poly(vinylidene fluoride-co-hexafluoropropene); poly(hydroxyvalerate); poly(L-lactic acid); poly(epsilon-caprolactone); poly(lactide-co-glycolide); poly(hydroxybutyrate); poly(hydroxybutyrate-co-valerate); polydioxanone; polyorthoester; polyanhydride; poly(glycolic acid); poly(D,L-lactic acid); poly(glycolic acid-co-trimethylene carbonate); polyphosphoester; poly-phosphoester urethane; poly(amino acids); cyanoacrylates; poly(trimethylene carbonate); poly(iminocarbonate); co-poly(ether-esters) (e.g. PEO/PLA); polyalkylene oxalates; polyphosphazenes; biomolecules, such as fibrin, fibrinogen, cellulose, starch, collagen and hyaluronic acid; polyurethanes; silicones; polyesters; polyolefins; polyisobutylene and ethylene-alpha-olefin copolymers; acrylic polymers and copolymers; vinyl halide polymers and copolymers, such as polyvinyl chloride; polyvinyl ethers, such as polyvinyl methyl ether; polyvinylidene halides, such as polyvinylidene fluoride and polyvinylidene chloride; polyacrylonitrile; polyvinyl ketones; polyvinyl aromatics, such as polystyrene; polyvinyl esters, such as polyvinyl acetate; copolymers of vinyl monomers with each other and olefins, such as ethylene-methyl methacrylate copolymers, acrylonitrile-styrene copolymers, ABS resins, and ethylene-vinyl acetate copolymers; polyamides, such as Nylon 66 and polycaprolactam; alkyd resins; polycarbonates; polyoxymethylenes; polyimides; polyethers; epoxy resins; polyurethanes; rayon; rayon-triacetate; cellulose acetate; cellulose butyrate; cellulose acetate butyrate; cellophane; cellulose nitrate; cellulose propionate; cellulose ethers; and carboxymethyl cellulose.

EVAL is functionally a very suitable choice of polymer. EVAL copolymer refers to copolymers comprising residues of both ethylene and vinyl alcohol monomers. One of ordinary skill in the art understands that ethylene vinyl alcohol copolymer may also be a terpolymer so as to include small amounts of additional monomers, for example less than about five (5) mole percentage of styrenes, propylene, or other suitable monomers. Ethylene vinyl alcohol copolymers are available commercially from companies such as Aldrich Chemical Company, Milwaukee, Wis., or EVAL Company of America, Lisle, Ill., or can be prepared by conventional polymerization procedures that are well known to one of ordinary skill in the art.

Poly(butylmethacrylate) ("PBMA") and ethylene-vinyl acetate copolymers can also be especially suitable polymers for the reservoir layer. In one embodiment, the polymer in the reservoir coating is a mixture of PBMA and an ethylene-vinyl acetate copolymer.

KRATON G-1650 is also a suitable polymer. KRATON is manufactured by Shell Chemicals Co. of Houston, Tex., and is a three block copolymer with hard polystyrene end blocks and a thermoplastic elastomeric poly(ethylene-butylene) soft middle block. KRATON G-1650 contains about 30 mass % of polystyrene blocks.

Representative examples of solvents that can be combined with the polymer and active agent include chloroform, acetone, water (buffered saline), dimethylsulfoxide, propylene glycol methyl ether, iso-propylalcohol, n-propylalcohol, methanol, ethanol, tetrahydrofuran, dimethylformamide, dimethylacetamide, benzene, toluene, xylene, hexane, cyclohexane, pentane, heptane, octane, nonane, decane, decalin, ethyl acetate, butyl acetate, isobutyl acetate, isopropyl acetate, butanol, diacetone alcohol, benzyl alcohol, 2-butanone, cyclohexanone, dioxane, methylene chloride, carbon tetrachloride, tetrachloroethylene, tetrachloro ethane, chlorobenzene, 1,1,1-trichloroethane, formamide, hexafluoroisopropanol, 1,1,1-trifluoroethanol, and hexamethyl phosphoramide and a combination thereof.

The active agent may be any substance capable of exerting a therapeutic or prophylactic effect in the practice of the present invention. Examples of such active agents include antiproliferative, antineoplastic, antiinflammatory, antiplatelet, anticoagulant, antifibrin, antithrombin, antimitotic, antibiotic, and antioxidant substances as well as combinations thereof. An example of an antiproliferative substance is actinomycin D, or derivatives and analogs thereof (manufactured by Sigma-Aldrich 1001 West Saint Paul Avenue, Milwaukee, Wis. 53233; or COSMEGEN available from Merck). Synonyms of actinomycin D include dactinomycin, actinomycin IV, actinomycin $I_1$, actinomycin $X_1$, and actinomycin $C_1$. Examples of antineoplastics include paclitaxel and docetaxel. Examples of antiplatelets, anticoagulants, antifibrins, and antithrombins include aspirin, sodium heparin, low molecular weight heparin, hirudin, argatroban, forskolin, vapiprost, prostacyclin and prostacyclin analogs, dextran, D-phe-pro-arg-chloromethylketone (synthetic antithrombin), dipyridamole, glycoprotein IIb/IIIa platelet membrane receptor antagonist, recombinant hirudin, thrombin inhibitor (available from Biogen), and 7E-3B® (an antiplatelet drug from Centocor). Examples of antimitotic agents include methotrexate, azathioprine, vincristine, vinblastine, fluorouracil, adriamycin, and mutamycin. Examples of cytostatic or antiproliferative agents include angiopeptin (a somatostatin analog from Ibsen), angiotensin converting enzyme inhibitors such as CAPTOPRIL (available from Squibb), CILAZAPRIL (available from Hoffman-LaRoche), or LISINOPRIL (available from Merck & Co., Whitehouse Station, N.J.), calcium channel blockers (such as Nifedipine), colchicine, fibroblast growth factor (FGF) antagonists, histamine antagonist, LOVASTATIN (an inhibitor of HMG-CoA reductase, a cholesterol lowering drug from Merck & Co.), monoclonal antibodies (such as PDGF receptors), nitroprusside, phosphodiesterase inhibitors, prostaglandin inhibitor (available form Glazo), Seramin (a PDGF antagonist), serotonin blockers, thioprotease inhibitors, triazolopyrimidine (a PDGF antagonist), and nitric oxide. Other therapeutic substances or agents that may be appropriate include alpha-interferon, genetically engineered epithelial cells, dexamethasone, estradiol, clobetasol propionate, cisplatin, insulin sensitizers, receptor tyrosine kinase inhibitors and carboplatin. Exposure of the composition to the active agent should not adversely alter the active agent's composition or characteristic. Accordingly, the particular active agent is selected for compatibility with the blended composition.

In one embodiment, rapamycin, or a functional or structural derivative such as 40-O-(2-hydroxy)ethyl-rapamycin can be used. The chemical structure for 40-O-(2-hydroxy)ethyl-rapamycin is as follows:

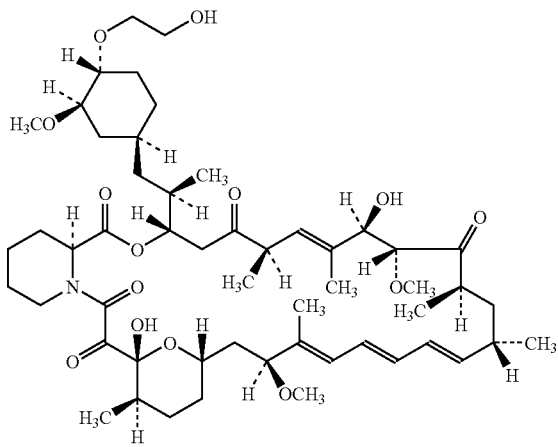

Analogs or derivatives of 40-O-(2-hydroxy)ethyl-rapamycin can also be used, examples of which include but are not limited to 40-O-(3-hydroxy)propyl-rapamycin and 40-O-[2-(2-hydroxy)ethoxy]ethyl-rapamycin.

40-O-(2-hydroxy)ethyl-rapamycin binds to the cytosolic immunophyllin FKBP12 and inhibits growth factor-driven cell proliferation, including that of T-cells and vascular smooth muscle cells. The actions of 40-O-(2-hydroxy)ethyl-rapamycin occur late in the cell cycle (i.e., late G1 stage) compared to other immunosuppressive agents such as tacrolimus or cyclosporine which block transcriptional activation of early T-cell-specific genes. Since 40-O-(2-hydroxy)ethyl-rapamycin can act as a potent anti-proliferative agent, it is believed that 40-O-(2-hydroxy)ethyl-rapamycin can be an effective agent to treat restenosis by being delivered to a local treatment site from a polymeric coated implantable device such as a stent.

The release rate of 40-O-(2-hydroxy)ethyl-rapamycin can be advantageously controlled by various methods and coatings as described herein. In particular, by using the methods and coatings of the present invention, the release rate of the 40-O-(2-hydroxy)ethyl-rapamycin, or analog or derivative thereof, can be less than about 50% in 24 hours.

The 40-O-(2-hydroxy)ethyl-rapamycin, or analog or derivative thereof, in the reservoir layer can be in the amount of about 50 µg to about 500 µg, more narrowly about 90 µg to about 350 µg, and the polymer can be in the amount of about 50 µg to about 1000 µg, more narrowly about 90 µg to about 500 µg. When the 40-O-(2-hydroxy)ethyl-rapamycin is blended with a polymer for the reservoir layer, the ratio of 40-O-(2-hydroxy)ethyl-rapamycin, or analog or derivative thereof, to polymer by weight in the reservoir layer can be about 1:2.8 to about 1.5:1.

The dosage or concentration of the active agent required to produce a therapeutic effect should be less than the level at which the active agent produces unwanted toxic effects and greater than the level at which non-therapeutic results are obtained. The dosage or concentration of the active agent required to inhibit the desired cellular activity of the vascular region, for example, can depend upon factors such as the particular circumstances of the patient; the nature of the trauma; the nature of the therapy desired; the time over which the ingredient administered resides at the vascular site; and if other bioactive substances are employed, the nature and type of the substance or combination of substances. Therapeutically effective dosages can be determined empirically, for example by infusing vessels from suitable animal model systems and using immunohistochemical, fluorescent or electron microscopy methods to detect the agent and its effects, or by conducting suitable in vitro studies. Standard pharmacological test procedures to determine dosages are understood by one of ordinary skill in the art.

Forming a Barrier Layer to Reduce the Rate of Release

In some coatings, the release rate of the active agent may be too high to be clinically useful. A barrier layer can reduce the rate of release or delay the time at which the active agent is released from the reservoir layer.

In accordance with one embodiment, the barrier layer can be applied on a selected region of the reservoir layer to form a rate reducing member. The barrier layer can be applied to the reservoir layer prior to or subsequent to the fluid treatment. If the barrier layer is applied to the reservoir layer prior to the fluid treatment, the solvent in the barrier layer should be allowed to evaporate to form a dry coating prior to application of the fluid. Similarly, if the barrier layer is applied to the reservoir layer subsequent to the fluid treatment, the barrier layer should be applied after the fluid has been allowed to evaporate from the coating.

The composition for the barrier layer can be substantially free of active agents. Alternatively, for maximum blood compatibility, compounds such as polyethylene glycol, heparin, heparin derivatives having hydrophobic counterions, or polyethylene oxide can be added to the barrier layer, or disposed on top of the barrier layer.

The choice of polymer for the barrier layer can be the same as the selected polymer for the reservoir. The use of the same polymer, as described for some of the embodiments, significantly reduces or eliminates any interfacial incompatibilities, such as lack of adhesion, which may exist in the employment of two different polymeric layers.

Polymers that can be used for a barrier layer include the examples of polymers listed above for the reservoir layer. Representative examples of polymers for the barrier layer also include polytetrafluoroethylene, perfluoro elastomers, ethylene-tetrafluoroethylene copolymer, fluoroethylene-alkyl vinyl ether copolymer, polyhexafluoropropylene, low density linear polyethylenes having high molecular weights, ethylene-olefin copolymers, atactic polypropylene, polyisobutene, polybutylenes, polybutenes, styrene-ethylene-styrene block copolymers, styrene-butylene-styrene block copolymers, styrene-butadiene-styrene block copolymers, and ethylene methacrylic acid copolymers of low methacrylic acid content.

EVAL is functionally a very suitable choice of polymer for the barrier layer. The copolymer can comprise a mole percent of ethylene of from about 27% to about 48%. Fluoropolymers are also a suitable choice for the barrier layer composition. For example, polyvinylidene fluoride (otherwise known as KYNAR, available from ATOFINA Chemicals, Philadelphia, Pa.) can be dissolved in acetone, methylethylketone, dimethylacetamide, and cyclohexanone, and can optionally be combined with EVAL to form the barrier layer composition. Also, solution processing of fluoropolymers is possible, particularly the low crystallinity varieties such as CYTOP available from Asahi Glass and TEFLON AF available from DuPont. Solutions of up to about 15% (w/w) are possible in perfluoro solvents, such as FC-75 (available from 3M under the brand name FLUORINERT), which are non-polar, low boiling solvents. Such volatility allows the solvent to be easily and quickly evaporated following the application of the polymer-solvent solution to the implantable device.

PBMA and ethylene-vinyl acetate copolymers can also be especially suitable polymers for the barrier layer. PBMA, for example, can be dissolved in a solution of xylene, acetone and HFE FLUX REMOVER (Techspray, Amarillo, Tex.). In another embodiment, the polymer in the barrier layer is PBMA or a mixture of PBMA and an ethylene-vinyl acetate copolymer.

Other choices of polymers for the rate-limiting membrane include, but are not limited to, ethylene-anhydride copolymers; and ethylene-acrylic acid copolymers having, for example, a mole % of acrylic acid of from about 2% to about 25%. The ethylene-anhydride copolymer available from Bynel adheres well to EVAL and thus would function well as a barrier layer over a reservoir layer made from EVAL. The copolymer can be dissolved in organic solvents, such as dimethylsulfoxide and dimethylacetamide. Ethylene vinyl acetate polymers can be dissolved in organic solvents, such as toluene and n-butyl acetate. Ethylene-acrylic acid copolymers can be dissolved in organic solvents, such as methanol, isopropyl alcohol, and dimethylsulfoxide.

Yet another choice of polymer for the rate-limiting membrane is a cross-linked silicone elastomer. Loose silicone and silicone with very low cross-linking are thought to cause an inflammatory biological response. However, it is believed that a thoroughly cross-linked silicone elastomer, having low levels of leachable silicone polymer and oligomer, is an essentially non-inflammatory substance. Silicone elastomers, such as Nusil MED-4750, MED-4755, or MED2-6640, having high tensile strengths, for example between 1200 psi and 1500 psi, will likely have the best durability during crimping, delivery, and expansion of a stent as well as good adhesion to a reservoir layer, e.g., EVAL or the surface of an implantable device.

The composition for a rate-reducing membrane or diffusion barrier layer can be prepared by the methods used to prepare a polymer solution as described above. The polymer can comprise from about 0.1% to about 35%, more narrowly from about 1% to about 20% by weight of the total weight of the composition, and the solvent can comprise from about 65% to about 99.9%, more narrowly from about 80% to about 98% by weight of the total weight of the composition. Selection of a specific weight ratio of the polymer and solvent is dependent on factors such as, but not limited to, the type of polymer and solvent employed, the type of underlying reservoir layer, and the method of application.

Forming a Primer Layer

The presence of an active agent in a polymeric matrix can interfere with the ability of the matrix to adhere effectively to the surface of the device. Increasing the quantity of the active agent reduces the effectiveness of the adhesion. High drug loadings in the coating can hinder the retention of the coating on the surface of the device. A primer layer can serve as a functionally useful intermediary layer between the surface of the device and an active agent-containing or reservoir coating. The primer layer provides an adhesive tie between the reservoir coating and the device—which, in effect, would also allow for the quantity of the active agent in the reservoir coating to be increased without compromising the ability of the reservoir coating to be effectively contained on the device during delivery and, if applicable, expansion of the device.

The primer composition can be prepared by adding a predetermined amount of a polymer to a predetermined amount of a compatible solvent. By way of example, and not limitation, the polymer can comprise from about 0.1% to about 35%, more narrowly from about 1% to about 20% by weight of the total weight of the composition, and the solvent can comprise from about 65% to about 99.9%, more narrowly from about 80% to about 98% by weight of the total weight of the primer composition. A specific weight ratio is dependent on factors such as the material from which the implantable device is made, the geometrical structure of the device, the choice of polymer-solvent combination, and the method of application.

Representative examples of polymers for the primer layer include, but are not limited to, polyisocyanates, such as triisocyanurate and polyisocyanate; polyethers; polyurethanes based on diphenylmethane diisocyanate; acrylates, such as copolymers of ethyl acrylate and methacrylic acid; titanates, such as tetra-iso-propyl titanate and tetra-n-butyl titanate; zirconates, such as n-propyl zirconate and n-butyl zirconate; silane coupling agents, such as 3-aminopropyltriethoxysilane and (3-glydidoxypropyl) methyldiethoxysilane; high amine content polymers, such as polyethyleneamine, polyallylamine, and polylysine; polymers with a high content of hydrogen bonding groups, such as polyethylene-co-polyvinyl alcohol, ethylene vinyl acetate, and melamine formaldehydes; and unsaturated polymers and prepolymers, such as polycaprolactone diacrylates, polyacrylates with at least two acrylate groups, and polyacrylated polyurethanes. With the use of unsaturated prepolymers, a free radical or UV initiator can be added to the composition for the thermal or UV curing or cross-linking process, as is understood by one of ordinary skill in the art.

Representative examples of polymers that can be used for the primer material also include those polymers that can be used for the reservoir layer as described above. The use of the same polymer significantly reduces or eliminates any interfacial incompatibilities, such as lack of an adhesive tie or bond, which may exist with the employment of two different polymeric layers.

EVAL is a very suitable choice of polymer for the primer layer. The copolymer possesses good adhesive qualities to the surface of a stent, particularly stainless steel surfaces, and has illustrated the ability to expand with a stent without any significant detachment of the copolymer from the surface of the stent. The copolymer can comprise a mole percent of ethylene of from about 27% to about 48%.

Methods For Applying the Compositions to the Device

Application of the composition can be by any conventional method, such as by spraying the composition onto the prosthesis or by immersing the prosthesis in the composition. Operations such as wiping, centrifugation, blowing, or other web-clearing acts can also be performed to achieve a more uniform coating. Briefly, wiping refers to physical removal of excess coating from the surface of the stent; centrifugation refers to rapid rotation of the stent about an axis of rotation; and blowing refers to application of air at a selected pressure to the deposited coating. Any excess coating can also be vacuumed off the surface of the device.

If the optional primer layer is to be formed on the device, the primer composition can first be applied to a designated region of the surface of the device. The solvent(s) is removed from the composition by allowing the solvent(s) to evaporate. The evaporation can be induced by heating the device at a predetermined temperature for a predetermined period of time. For example, the device can be heated at a temperature of about 60° C. for about 10 minutes to about 24 hours. The heating can be conducted in an anhydrous atmosphere and at ambient pressure and should not exceed the temperature which would adversely affect the active agent. The heating can also be conducted under a vacuum condition.

The composition containing the active agent can be applied to a designated region of the surface of the device. If the optional primer layer has been formed on the surface of the device, active agent-containing composition can be applied to the dry primer layer. Thereafter, the solvent(s) can be removed from the reservoir layer as described above for the primer layer.

Examples of the Device

Examples of implantable devices for the present invention include self-expandable stents, balloon-expandable stents, stent-grafts, grafts (e.g., aortic grafts), artificial heart valves, cerebrospinal fluid shunts, pacemaker electrodes, and endocardial leads (e.g., FINELINE and ENDOTAK, available from Guidant Corporation, Santa Clara, Calif.). The underlying structure of the device can be of virtually any design. The device can be made of a metallic material or an alloy such as, but not limited to, cobalt chromium alloy (ELGILOY), stainless steel (316L), high nitrogen stainless steel, e.g., BIODUR 108, cobalt chrome alloy L-605, "MP35N," "MP20N," ELASTINITE (Nitinol), tantalum, nickel-titanium alloy, platinum-iridium alloy, gold, magnesium, or combinations thereof. "MP35N" and "MP20N" are trade names for alloys of cobalt, nickel, chromium and molybdenum available from Standard Press Steel Co., Jenkintown, Pa. "MP35N" consists of 35% cobalt, 35% nickel, 20% chromium, and 10% molybdenum. "MP20N" consists of 50% cobalt, 20% nickel, 20% chromium, and 10% molybdenum. Devices made from bioabsorbable or biostable polymers could also be used with the embodiments of the present invention.

The embodiments of the present invention may be particularly useful for the coatings of small vessel stents. Small vessels stents can be generally categorized as having inner diameters of less than 2.5 mm in an expanded state. Because of their small size, small vessel stents offer unique challenges for drug delivery. In particular, as compared to conventionally sized stents, small vessel stents have a greater surface:volume ratio. Therefore, when a small vessel stent is inserted into a biological lumen, the vessel tissue surrounding a small vessel stent is exposed to a greater concentration of polymer. The present invention can be used to reduce the amount of polymer that is needed on the stent structure and still maintain an efficacious release rate. The present invention, therefore, can reduce the risk of an inflammatory response by the vessel tissue when small stents are used as a drug delivery device in small vessels.

Method of Use

In accordance with the above-described method, the active agent can be applied to a device, e.g., a stent, retained on the device during delivery and released at a desired control rate and for a predetermined duration of time at the site of implantation. A stent having the above-described coating layers is useful for a variety of medical procedures, including, by way of example, treatment of obstructions caused by tumors in bile ducts, esophagus, trachea/bronchi and other biological passageways. A stent having the above-described coating layers is particularly useful for treating occluded regions of blood vessels caused by abnormal or inappropriate migration and proliferation of smooth muscle cells, thrombosis, and restenosis. Stents may be placed in a wide array of blood vessels, both arteries and veins. Representative examples of sites include the iliac, renal, and coronary arteries.

Briefly, an angiogram is first performed to determine the appropriate positioning for stent therapy. Angiography is typically accomplished by injecting a radiopaque contrasting agent through a catheter inserted into an artery or vein as an x-ray is taken. A guidewire is then advanced through the lesion or proposed site of treatment. Over the guidewire is passed a delivery catheter, which allows a stent in its collapsed configuration to be inserted into the passageway. The delivery catheter is inserted either percutaneously, or by surgery, into the femoral artery, brachial artery, femoral vein, or brachial vein, and advanced into the appropriate blood vessel by steering the catheter through the vascular system under fluoroscopic guidance. A stent having the above-described coating layers may then be expanded at the desired area of treatment. A post insertion angiogram may also be utilized to confirm appropriate positioning.

EXAMPLES

The embodiments of the invention will be illustrated by the following set forth examples which are being given by way of illustration only and not by way of limitation. All parameters and data are not be construed to unduly limit the scope of the embodiments of the invention.

Example 1

18 mm VISION stents (available from Guidant Corporation) were coated by spraying a 2% (w/w) solution of polybutylmethacrylate ("PBMA") mixed with a solvent having 60% acetone and 40% xylene (w/w). The solvent was removed by baking at 80° C. for 30 minutes. The target primer weight was 160 µg. A solution of 2% (w/w) PBMA and 40-O-(2-hydroxy)ethyl-rapamycin in a mixture of 60% acetone and 40% xylene (w/w) was spray coated onto the stents. The drug to polymer ratio for the coating was 1.25 to 1, with a target reservoir coating weight of 288 µg. The target drug loading was 160 µg. The stents were then baked at 50° C. for 2 hours to produce dry coatings.

Example 2

The stents were separated into two test groups. Group A served as the control group, and Group B was exposed to a fluid treatment. In particular, the stents of Group B were sprayed with a solution of pure ethanol for five spray cycles. In particular, the following Table 4 lists the spray process parameters that were used to conduct the fluid treatment process:

TABLE 4

| Parameter | Set Value | Units |
|---|---|---|
| Spray Head | | |
| Spray nozzle temperature | 26 ± 2 | ° C. |
| Atomization pressure (non-activated) | 15 ± 2.5 | psi |
| Distance from spray nozzle to coating mandrel pin | 10-12 | mm |
| Solution barrel pressure | 2.5 | psi |
| Needle valve lift pressure | 80 ± 10 | psi |
| Heat Nozzle | | |
| Temperature | 26 ± 2 | ° C. |
| Air Pressure | 12-15 | psi |
| Distance from heat nozzle to coating mandrel pin | 10-15 | mm |

The stents of Group B were then baked to essentially remove the ethanol.

Example 3

The drug-coated stents were placed on stent holders of a Vankel Bio-Dis release rate tester (Vankel, Inc., Cary, N.C.). 3 stents from each test group were dipped into an artificial medium for about 1 hour to extract the 40-O-(2-hydroxy)ethyl-rapamycin from the stent coatings. The artificial medium included a phosphate buffer saline solution (10 mM, pH 7.4) and 1% TRITON X-100 (Sigma Corporation) which stabilizes the 40-O-(2-hydroxy)ethyl-rapamycin in the testing solution. Each stent was tested in a separate testing solution to prevent cross-contamination. After extraction, each of the solutions was separately analyzed for the amount of drug released from the stent coatings by using an HPLC process. The HPLC system consisted of a Waters 2690 system. After the drug solutions were analyzed by HPLC, the results were quantified by comparing the release rate results with a reference standard.

Each of the stents were then dipped in fresh extraction solutions for another 6 hours (7 hours total). The solutions were analyzed by HPLC as described above. Finally, the stents were dipped in fresh extraction solutions for another 17 hours (24 hours total). The solutions were again analyzed by HPLC as described above.

Next, the total drug content of the coatings was determined. First, 3 stents from each test group were placed in volumetric flasks. Each stent was placed in a separate flask. An appropriate amount of the extraction solvent acetonitrile with 0.02% butylated hydroxytoluene as a protectant was added to each flask. The flasks were sonicated for a sufficient time to extract all of the drug from the reservoir regions. Then, the solution in the flasks was filled to mark with the solvent solution. The drug solutions for each stent were separately analyzed by HPLC. The HPLC release rate results were quantified by comparing the results with a reference standard. The total drug content of the stents was then calculated.

The drug release profile could then be generated by plotting cumulative drug released in the medium vs. time. The percentage of drug released at a specific time was determine by comparing the cumulative drug released with the total content data. The results demonstrate that the fluid treatment process substantially reduces the release rate of the active agent. The results for the total content analysis are summarized in Table 5, the drug release profile is summarized in Table 6, and the release rate for each test group is summarized in Table 7.

TABLE 5

| | Group A | | | Group B | | |
|---|---|---|---|---|---|---|
| | Stent 1 | Stent 2 | Stent 3 | Stent 1 | Stent 2 | Stent 3 |
| Theoretical Total Recovery (µg) | 149.4 | 174.4 | 166.1 | 165.0 | 163.3 | 166.1 |
| Total Recovered (µg) | 142.4 | 161.6 | 150.7 | 128.2 | 135.0 | 133.1 |
| % Recovered | 95 | 93 | 91 | 78 | 83 | 80 |

TABLE 6

| | Group A (µg released) | | | Group B (µg released) | | |
|---|---|---|---|---|---|---|
| | Stent 1 | Stent 2 | Stent 3 | Stent 1 | Stent 2 | Stent 3 |
| Time (hours) | | | | | | |
| 1 | 34.93 | 30.37 | 36.89 | 7.82 | 3.67 | 1.88 |
| 7 | 55.44 | 54.30 | 62.03 | 25.50 | 9.92 | 5.31 |
| 24 | 74.55 | 82.69 | 89.62 | 46.40 | 16.84 | 10.14 |
| Average for Group (24 hours) | | 82.29 | | | 24.46 | |
| Standard Deviation for Group | | 7.54 | | | 19.29 | |

TABLE 7

| | Group A (% of drug released) | | | Group B (% of drug released) | | |
|---|---|---|---|---|---|---|
| | Stent 1 | Stent 2 | Stent 3 | Stent 1 | Stent 2 | Stent 3 |
| Time (hours) | | | | | | |
| 1 | 25 | 19 | 24 | 5 | 2 | 1 |
| 7 | 39 | 34 | 41 | 17 | 7 | 4 |
| 24 | 52 | 51 | 59 | 31 | 11 | 7 |
| Average for Group (24 hours) | | 54.35 | | | 16.24 | |
| Standard Deviation for Group | | 4.49 | | | 12.80 | |

Example 4

The following experiment was conducted in order to obtain information on how the fluid treatment process could affect polymer morphology. Pellets of poly(vinylidene fluoride-co-hexafluoropropene) (SOLEF 21508, available from Solvay Solexis PVDF, Thorofare, N.J.) were placed in a sealable container. The treatment fluid, ethyl acetate, was added to the container at a 1:7 polymer:fluid ratio (w/w) and the container was sealed. The contents of the container were agitated at room temperature for about five hours by using a magnetic stir bar. Upon visible inspection, the pellets about doubled in size, indicating that the fluid caused the polymer to swell. After the treatment, the polymer pellets were removed from the container and dried at 50° C. overnight.

Figure 5A:
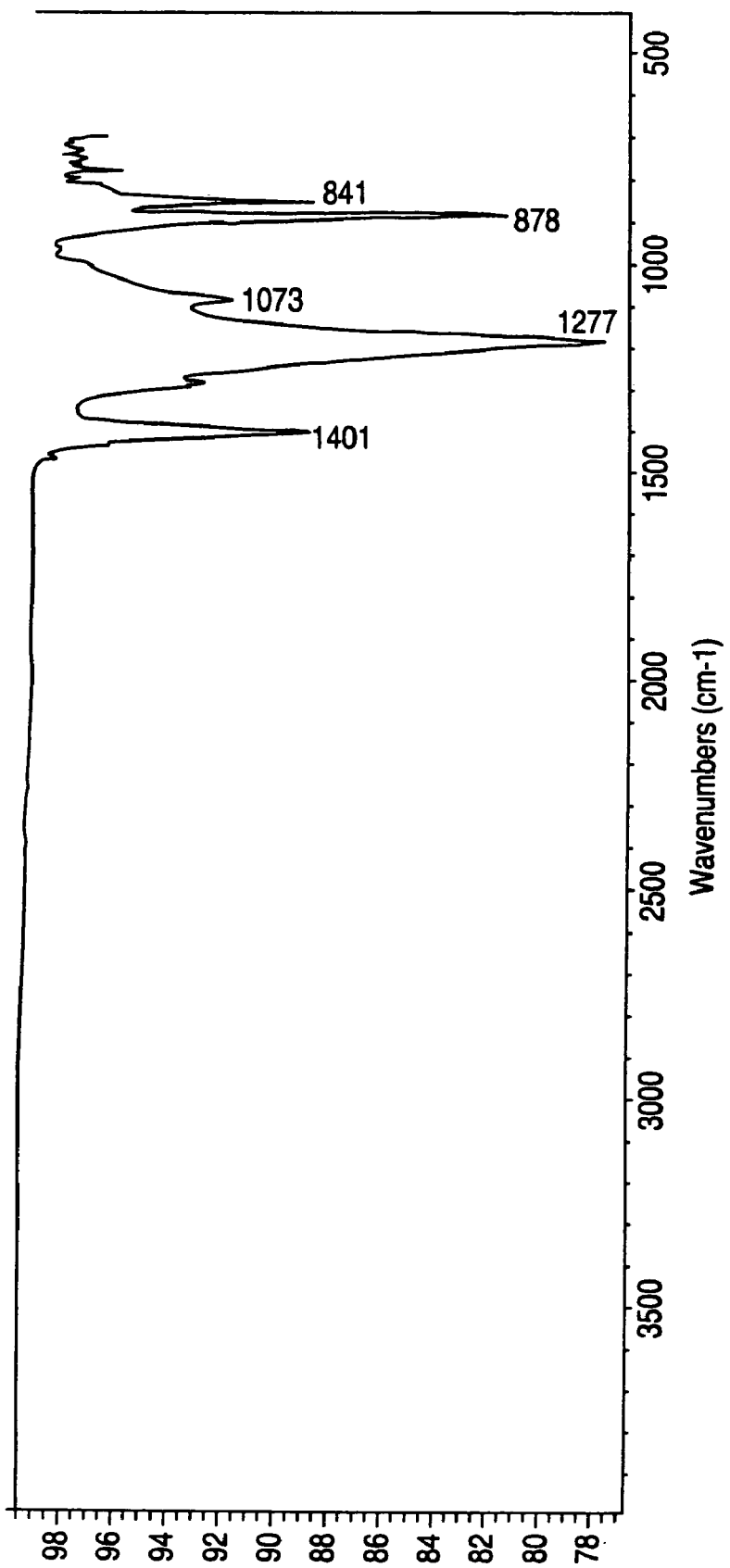
FIGS. 5A and 5B are Fourier Transform Infrared spectrographs that are referred to in Example 4.
Figure 5B:
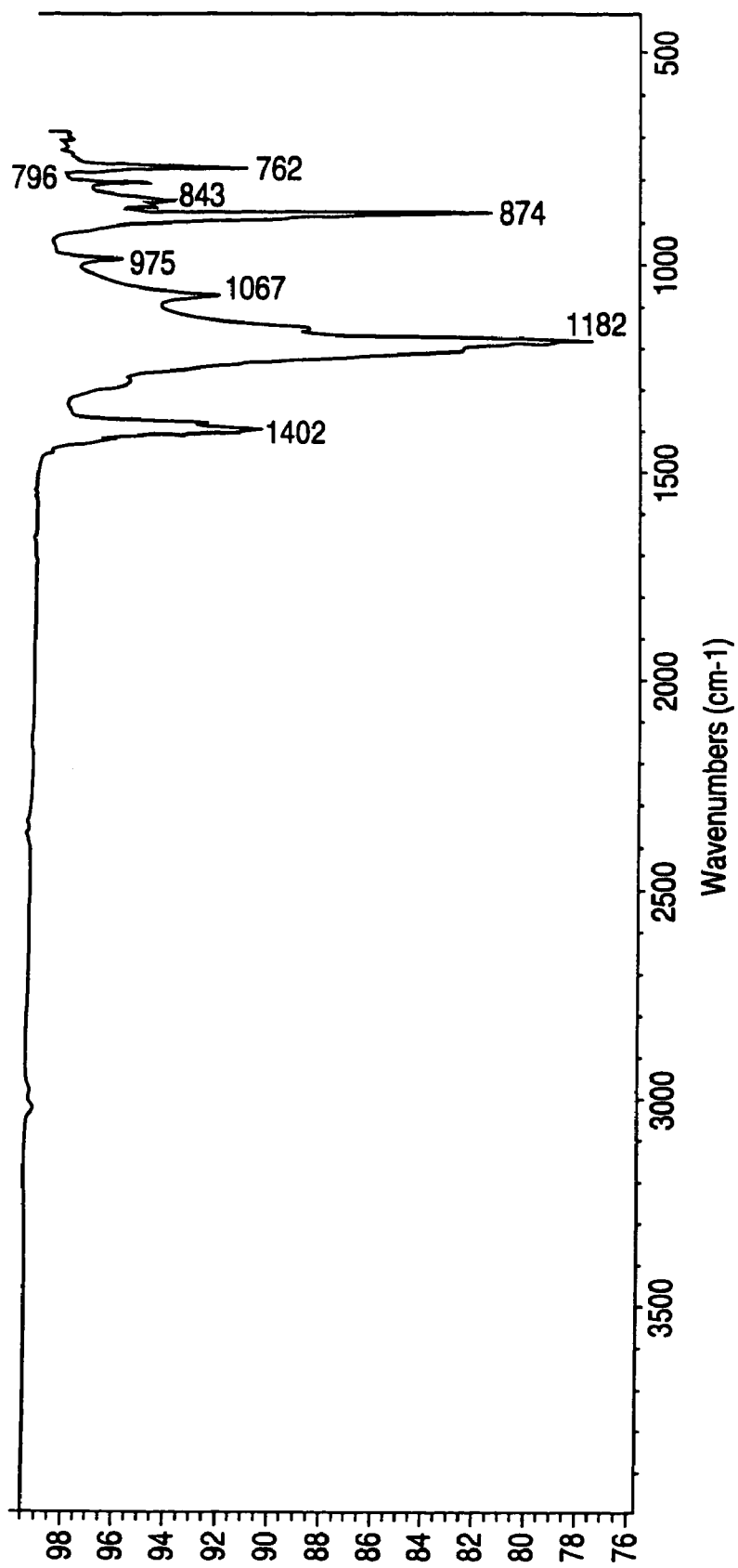

A Fourier Transform Infrared (FTIR) analysis was conducted on a control group (i.e., pellets of poly(vinylidene fluoride-co-hexafluoropropene) which had not been exposed to the fluid treatment). The results for the control group are illustrated in the spectrograph of FIG. 5A. An FTIR analysis was also conducted on the pellets exposed to the fluid treatment. The results for the fluid treatment group are illustrated in the spectrograph of FIG. 5B. The spectra of FIGS. 5A and 5B are substantially similar, except that a peak near 975 cm$^{-1}$ appears for the polymer treated with the fluid as shown in FIG. 5B.

It was confirmed by conducting a differential scanning calorimetry (DSC) experiment that the peak near 975 cm$^{-1}$ indicated an increase in percent crystallinity for the polymer. In particular, it was determined that the polymer treated with the fluid had a melting enthalpy of about 35 J/gram, whereas a control sample of polymer that was untreated had a melting enthalpy of about 24 J/gram. The increased melting enthalpy of the treated polymer indicated an increase in percent crystallinity.

Example 5

18 mm VISION stents (available from Guidant Corporation) are coated by spraying a 2% (w/w) solution of poly(vinylidene fluoride-co-hexafluoropropene) (e.g., SOLEF 21508) and 40-O-(2-hydroxy)ethyl-rapamycin mixed with a solvent having 30:70 acetone/cyclohexanone (w/w). The drug to polymer ratio for the coating is 1.25 to 1. The target drug loading is 160 μg. The solvent is removed by baking at 50° C. for 2 hours to produce a dry drug coating. Next, the stents are immersed in a hydrofluoroether solvent (e.g., NOVEC HFE7200, ethoxynonafluorobutane ($C_4F_9OC_2H_5$), available from 3M, St. Paul, Minn.) for five minutes for a fluid treatment. The stents are then removed from the hydrofluoroether solvent and baked to remove essentially all of the fluid.

Example 6

18 mm VISION stents (available from Guidant Corporation) are coated by spraying a 2% (w/w) solution of PBMA mixed with a solvent having 60% acetone and 40% xylene (w/w). The solvent is removed by baking at 80° C. for 30 minutes. The target primer weight is 160 μg. A solution of 2% (w/w) PBMA and 40-O-(2-hydroxy)ethyl-rapamycin in a mixture of 60% acetone and 40% xylene (w/w) is spray coated onto the stents. The drug to polymer ratio for the coating is 1.25 to 1, with a target reservoir coating weight of about 288 μg. The target drug loading is 160 μg. The stents are then baked at 50° C. for 2 hours to produce dry coatings. Next, the stents are sprayed with acetone for five spray cycles. The acetone is allowed to evaporate to remove essentially all of the fluid from the coatings.

While particular embodiments of the present invention have been shown and described, it will be obvious to those skilled in the art that changes and modifications can be made without departing from this invention in its broader aspects. Therefore, the appended claims are to encompass within their scope all such changes and modifications as fall within the true spirit and scope of this invention.

What is claimed is:

1. A method of manufacturing a drug delivery implantable medical device, comprising:
    applying a composition to an implantable medical device, the composition including a polymer, an active agent and a solvent;
    allowing the solvent to evaporate to form a dry coating, the dry coating comprising less than about 2% residual fluid content (w/w);
    applying a fluid to the dry coating, the fluid being substantially or completely free from any polymer; and
    removing the fluid from the coating.

2. The method of claim 1, wherein fluid is substantially or completely free from any active agents.

3. The method of claim 1, wherein the active agent is at least partially soluble in the fluid.

4. The method of claim 1, additionally comprising prior to applying the composition, forming a primer layer on a surface of the implantable medical device.

5. The method of claim 1, additionally comprising forming a barrier layer on the dry coating wherein the application of the fluid is performed prior to forming the barrier layer.

6. The method of claim 1, wherein the device is a stent.

7. The method of claim 1, wherein the polymer comprises an ethylene vinyl alcohol copolymer, an ethylene-vinyl acetate copolymer, poly(vinylidene fluoride-co-hexafluoropropene), poly(butylmethacrylate), or a combination of the same.

8. The method of claim 1, wherein the dry coating comprises less than about 1% residual fluid content (w/w).

9. The method of claim 1, wherein the active agent is rapamycin, 40-O-(2-hydroxy)ethyl-rapamycin, paclitaxel, docetaxel, or a functional analog or structural derivative thereof.

10. The method of claim 1, wherein subsequent to the act of applying the fluid the total content of the active agent in the coating is at least 80% of the total content of the active agent in the coating prior to application of the fluid.

11. The method of claim 1, wherein the duration of exposure of the fluid is sufficient to decrease the release rate of the active agent from the coating after the coating has been implanted into a biological lumen.

12. The method of claim 1, wherein applying the fluid includes spraying the fluid onto the coating or immersing the device into a bath of fluid.

13. The method of claim 12, wherein the device is immersed for about 30 minutes to about twelve hours.

14. The method of claim 1, wherein the fluid is selected from the group consisting of chloroform, acetone, water, dimethylsulfoxide, propylene glycol methyl ether, iso-propylalcohol, n-propylalcohol, methanol, ethanol, tetrahydrofuran, dimethylformamide, dimethylacetamide, benzene, toluene, xylene, hexane, cyclohexane, pentane, heptane, octane, nonane, decane, decalin, ethyl acetate, butyl acetate, isobutyl acetate, isopropyl acetate, butanol, diacetone alcohol, benzyl alcohol, 2-butanone, cyclohexanone, dioxane, methylene chloride, carbon tetrachloride, tetrachloroethylene, tetrachloroethane, chlorobenzene, 1,1,1-trichloroethane, formamide, hexafluoroisopropanol, 1,1,1-trifluoroethanol, acetonitrile, hexamethyl phosphoramide and a combination thereof.

15. The method of claim 1, wherein the fluid is only applied to a portion of the device along the length of the device.

16. The method of claim 1, wherein the solvent and the fluid are different.

17. The method of claim 1, wherein subsequent to the removal of the fluid, the release rate of the active agent is less than about 30% in 24 hours.

18. The method of claim 1, wherein the temperature of the fluid is greater than room temperature.

19. The method of claim 1, wherein the temperature of the fluid is equal to or greater than the glass transition temperature of the polymer.

20. The method of claim 1, wherein the application of the fluid to the dry coating causes the percent crystallinity of the polymer in the coating to increase.

21. The method of claim 1, wherein the polymer is a blend of two or more polymers.

22. The method of claim 1, wherein the polymer is a semicrystalline polymer having about 10 to 75 percent crystallinity prior to the application of the fluid.

23. The method of claim 1, wherein the polymer is a block copolymer or a graft copolymer.

24. The method of claim 1, wherein the polymer exhibits two or more glass transition temperatures, and wherein the temperature of the fluid is equal to or greater than the lowest exhibited glass transition temperature of the polymer.

25. The method of claim 1, wherein the polymer exhibits two or more glass transition temperatures, and wherein the temperature of the fluid is equal to or greater than the highest exhibited glass transition temperature of the polymer.

26. A method of manufacturing a stent coating, comprising:
applying a composition to a stent, the composition including a semicrystalline polymer and a solvent;
allowing the solvent to evaporate to form a dry coating, the dry coating comprising less than about 2% residual fluid content (w/w); and
exposing the coating to a fluid for a sufficient duration to increase the crystallinity of the polymer in at least a portion of the coating, the fluid being substantially or completely free from any polymer; and
removing the fluid from the coating.

27. The method of claim 26, wherein the polymer has about 10 to 75 percent crystallinity prior to the act of exposing.

28. The method of claim 26, wherein the polymer comprises an ethylene vinyl alcohol copolymer or poly(vinylidene fluoride-co-hexafluoropropene).

29. The method of claim 26, wherein the dry coating comprises less than about 1% residual fluid content (w/w).

30. The method of claim 26, wherein exposing the coating to a fluid includes immersing the stent into a bath of fluid.

31. The method of claim 30, wherein the stent is immersed for about 30 minutes to about twelve hours.

32. The method of claim 1, wherein the polymer comprises a polyvinyl aromatic polymer.

33. The method of claim 26, wherein the polymer comprises a polyvinyl aromatic polymer.

34. The method of claim 26 wherein the composition further comprises an active agent.

35. The method of claim 1, wherein the fluid is completely free from any polymer.

36. The method of claim 1, wherein the fluid is completely free from any polymer and is substantially or completely free from the active agent.

37. The method of claim 1, wherein the fluid is completely free from any polymer and is completely free from the active agent.

38. The method of claim 1, wherein the fluid is completely free from the active agent.

39. The method of claim 1, wherein the fluid is substantially free from the active agent.

40. The method of claim 26, wherein the fluid is completely free from any polymer.

41. The method of claim 26, wherein the fluid is substantially free from an active agent.

42. The method of claim 26, wherein the fluid is completely free from an active agent.

43. The method of claim 1, wherein the composition forms a reservoir layer and wherein the dry coating includes a barrier layer formed over the reservoir layer prior to application of the fluid.

44. The method of claim 1, wherein the fluid is removed by evaporation.

45. The method of claim 26, wherein the fluid is removed by evaporation.

46. The method of claim 26, wherein the fluid is completely free of any polymer and is completely free from an active agent.

* * * * *